(12) United States Patent
Kii et al.

(10) Patent No.: US 11,954,888 B2
(45) Date of Patent: Apr. 9, 2024

(54) DEVICE, MICROSCOPE DEVICE, METHOD, AND PROGRAM

(71) Applicant: NIKON CORPORATION, Tokyo (JP)

(72) Inventors: Hiroaki Kii, Kawasaki (JP); Shinichi Takayama, Tokyo (JP)

(73) Assignee: NIKON CORPORATION, Tokyo (JP)

( * ) Notice: Subject to any disclaimer, the term of this patent is extended or adjusted under 35 U.S.C. 154(b) by 675 days.

(21) Appl. No.: 17/130,294

(22) Filed: Dec. 22, 2020

(65) Prior Publication Data

US 2021/0125335 A1    Apr. 29, 2021

Related U.S. Application Data

(63) Continuation of application No. PCT/JP2018/024676, filed on Jun. 28, 2018.

(51) Int. Cl.
| | |
|---|---|
| *G06T 7/90* | (2017.01) |
| *G06T 7/00* | (2017.01) |
| *G06V 10/56* | (2022.01) |
| *G06V 20/69* | (2022.01) |
| *G02B 21/36* | (2006.01) |

(52) U.S. Cl.
CPC .............. *G06T 7/90* (2017.01); *G06T 7/0012* (2013.01); *G06V 10/56* (2022.01); *G06V 20/695* (2022.01); *G06V 20/698* (2022.01); *G02B 21/365* (2013.01); *G06T 2207/10024* (2013.01); *G06T 2207/10056* (2013.01); *G06T 2207/30024* (2013.01)

(58) Field of Classification Search
CPC .................... G06T 7/90; G06T 7/0012; G06T 2207/10024; G06T 2207/10056; G06T 2207/30024; G06V 20/695; G06V 10/56; G06V 20/698; G06B 21/365
See application file for complete search history.

(56) References Cited

U.S. PATENT DOCUMENTS

| | | | |
|---|---|---|---|
| 7,060,445 B1 | 6/2006 | Dunlay | |
| 2016/0335767 A1* | 11/2016 | Matsumoto | .......... G06V 20/695 |
| 2017/0081628 A1* | 3/2017 | Matsubara | ............. C12M 41/46 |
| 2017/0169283 A1 | 6/2017 | Chen et al. | |
| 2020/0151909 A1* | 5/2020 | Yabusaki | .................. G06T 7/11 |

FOREIGN PATENT DOCUMENTS

| | | |
|---|---|---|
| EP | 3150692 A1 | 4/2017 |
| JP | 2008-261631 A | 10/2008 |
| JP | 2010-104301 A | 5/2010 |

(Continued)

OTHER PUBLICATIONS

Office Action issued in corresponding Japanese Application No. 2020-526819, dated Sep. 6, 2022, with English translation (10 pages).

(Continued)

*Primary Examiner* — John J Lee
(74) *Attorney, Agent, or Firm* — FOLEY & LARDNER LLP

(57) ABSTRACT

A device includes an image processing unit configured to calculate color information of at least one cell in a captured image and a determination unit configured to determine a cultured state of the cell on the basis of the color information calculated by the image processing unit.

16 Claims, 23 Drawing Sheets

(56) References Cited

FOREIGN PATENT DOCUMENTS

JP          2015-170047  A    9/2015
WO    WO-2015/182382  A1   12/2015

OTHER PUBLICATIONS

Notice of Reasons for Rejection issued for Japanese Application 2020-526819 dated Mar. 15, 2022.
International Search Report issued in corresponding application No. PCT/JP2018/024676 dated Oct. 2, 2018, with English translation.
Written Opinion issued in corresponding application No. PCT/JP2018/024676 dated Oct. 2, 2018, with English translation.
Kamao et al., "Objective Evaluation of the Degree of Pigmentation in Human Induced Pluripotent Stem Cell-Derived RPE", Investigative Ophthalmology & Visual Science (IOVS), Dec. 2014, vol. 55, No. 12 (pp. 8309-8318).
Office Action issued in corresponding United Kingdom Patent Application No. 2020540.7, dated Mar. 6, 2023 (5 pages).
JP Notice of reasons for Refusal for Japanese Appl. Ser. No. 2022-188327 dated Nov. 21, 2023 (8 pages).

* cited by examiner

ACQUIRED IMAGE

EXTRACTION OF CLUSTER OF CELLS

ACQUIRED IMAGE

EXTRACTION OF PAVING STONE-SHAPED CELLS

DEVICE, MICROSCOPE DEVICE, METHOD, AND PROGRAM

The present application is a continuation of PCT Application No. PCT/JP2018/024676, filed on Jun. 28, 2018, the entire contents of which are incorporated herein by reference.

TECHNICAL FIELD

Embodiments of the present invention relate to a device, a microscope device, a method, and a program.

BACKGROUND ART

In general, technology for evaluating a cultured state of cells has become basic technology in a wide range of fields including advanced medical fields such as regenerative medicine and drug screening. For example, in the field of regenerative medicine, there is a process of proliferating and differentiating cells in vitro. In this process, it is indispensable to accurately evaluate the cultured state of cells so that the success or failure of cell differentiation and the presence or absence of cancerization or infection of cells are managed. As an example, a method of evaluating cancer cells using a transcription factor as a marker has been disclosed (see, for example, Patent Document 1).

In the fields of research, drug discovery, and regenerative medicine, types of cells that exhibit color tones may be treated. For example, when cells that exhibit color tones are subjected to differentiation induction from stem cells such as embryonic stem (ES) cells and induced pluripotent stem (iPS) cells into target somatic cells and matured, it is important to evaluate a color tone in a differentiation induction process and a maturation process. For example, visual cells and retinal pigment epithelium (RPE) cells are known to exhibit colors ranging from red to brownish-red with the progress of growth.

In current cell manufacturing sites, process management in which a worker visually evaluates a change in the color tone of all the cells in a vessel and a worker determines a degree of differentiation induction and a degree of maturation is performed.

CITATION LIST

Patent Literature

[Patent Document 1]
U.S. Pat. No. 7,060,445

SUMMARY OF INVENTION

Technical Problem

The present invention has been made to solve the above-described problems and an objective the present invention is to provide a device, a microscope including the device, a method, and a program capable of determining cell growth with respect to a type of cell exhibiting a color tone according to the progress of growth.

Solution to Problem

According to an aspect of the present invention for solving the above-described problems, there is provided a device including: an image processing unit configured to calculate color information of at least one cell in a captured image; and a determination unit configured to determine a cultured state of the cell on the basis of the color information calculated by the image processing unit.

According to an aspect of the present invention, there is provided a microscope device including: the device; and a microscope configured to provide the device with an image of the subject.

According to an aspect of the present invention, there is provided a method to be executed by the device, the method including: calculating color information of at least one cell in a captured image; and determining a cultured state of the cell on the basis of the calculated color information.

According to an aspect of the present invention, there is provided a program for causing a device to: calculate color information of at least one cell in a captured image; and determine a cultured state of the cell on the basis of the calculated color information.

Advantageous Effects of Invention

According to embodiment of the present invention, it is possible to determine cell growth with respect to a type of cell exhibiting a color tone according to the progress of growth.

DESCRIPTION OF EMBODIMENTS

First Embodiment

Figure 1:
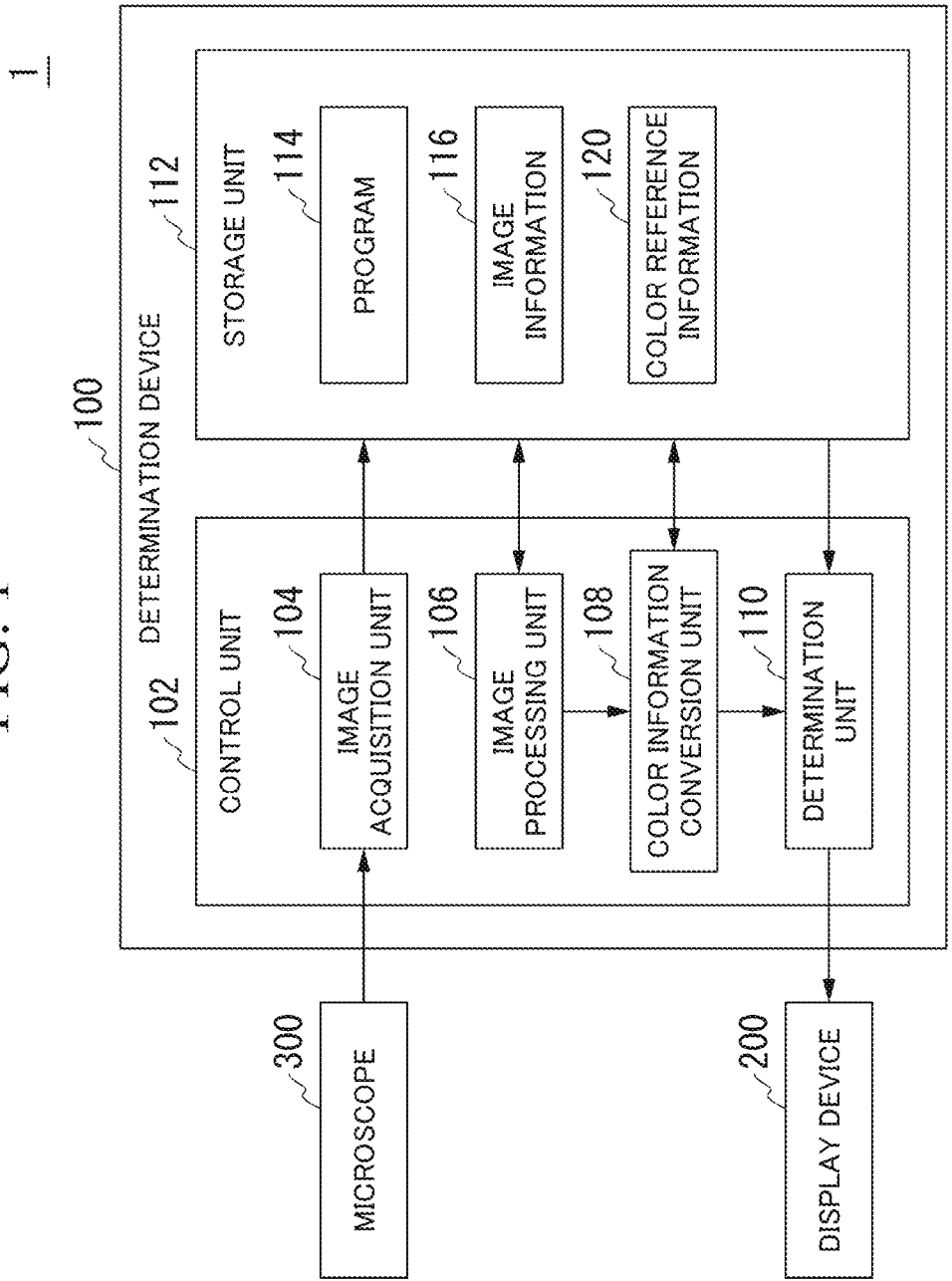
FIG. 1 is a diagram showing a determination system according to the present embodiment.

Hereinafter, a determination system according to an embodiment of the present invention will be described with reference to the drawings. FIG. 1 shows a determination system 1 according to the present embodiment. The determination system 1 includes a determination device 100, a display device 200, and a microscope 300.

The determination device 100 acquires an enlarged image of a subject S provided by the microscope 300. After the enlarged image of the subject S is acquired, the determination device 100 determines whether or not the subject S has grown normally on the basis of a color of the subject S included in an image obtained by performing image processing on an enlarged image of the subject S with reference to color information in one or more growth processes of cells whose colors change with the progress of growth. Hereinafter, cells whose colors change with the progress of growth are referred to as "sample cells."

Here, color information in one or more growth processes of the sample cells is pre-stored in the determination device 100. The determination device 100 displays a result of determining whether or not the subject S has grown normally on the display device 200. According to this configuration, the determination device 100 automatically evaluates whether or not the subject S has grown normally.

<Microscope>

Either one of a bright-field microscope and a phase-contrast microscope can be applied as the microscope 300. The bright-field microscope utilizes the fact that there is contrast between images of transmitted light because a light absorption rate is different between parts of the subject S when the subject S is irradiated with uniform incident light. The phase-contrast microscope is an optical microscope that converts a phase difference between light rays into contrast for observation. A case in which the phase-contrast microscope is used as an example in the determination system 1 according to the present embodiment will be described. Here, the present invention can also be applied when the bright-field microscope is used in the determination system 1.

<Configuration of Phase-Contrast Microscope>

Figure 2:
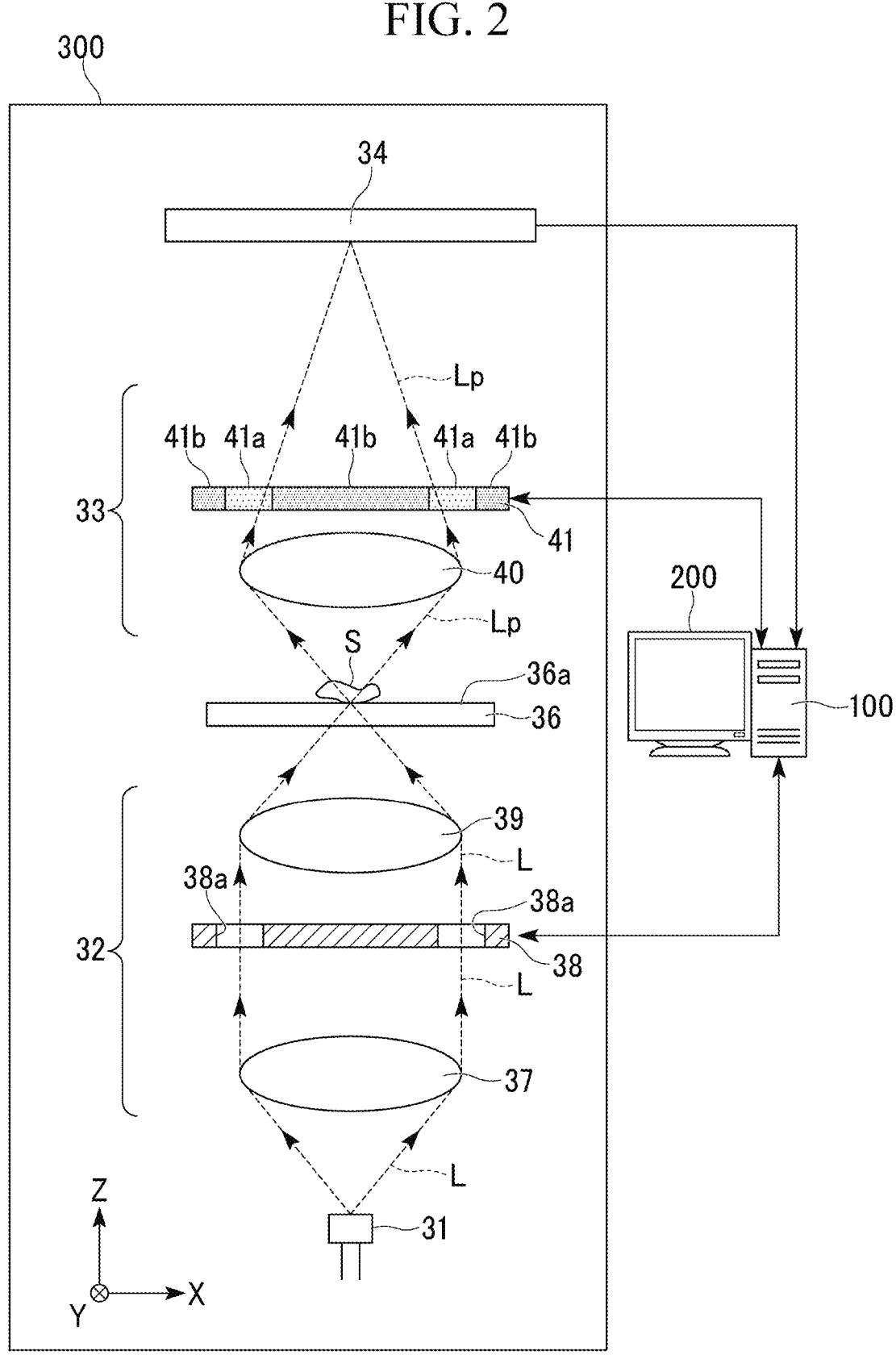
FIG. 2 is a diagram showing an example of a microscope.

FIG. 2 shows a configuration of the phase-contrast microscope. In FIG. 2, the determination device 100 and the display device 200 are also shown in addition to the phase-contrast microscope. A phase-contrast microscope device radiates illumination light L to the subject S to be observed and converts a phase difference of transmitted light Lp from the subject S into a contrast difference to obtain an enlarged image of the subject S.

The phase-contrast microscope device includes a light source 31 that emits the illumination light L; an illumination optical system 32 that radiates the illumination light L from the light source 31 to the subject S; an image forming optical system 33 that forms an image of the transmitted light Lp from the subject S; and a solid-state imaging element 34 that receives the transmitted light Lp whose image is formed by the image forming optical system 33 and converts the received transmitted light Lp into an electrical signal to generate an image of the subject S.

A stage 36 is disposed between the illumination optical system 32 and the image forming optical system 33.

The stage 36 has a placement surface 36a on which the subject S is placed. Also, the stage 36 is subjected to a movement operation in two directions (an X-axis direction and a Y-axis direction shown in FIG. 2) orthogonal to each other within a plane. Thereby, the stage 36 can arbitrarily change an observation position of the subject S. Further, the stage 36 may be configured to be subjected to a movement operation in a height direction (the Z-axis direction shown in FIG. 2).

Also, as described in the following, an optical axis (a central axis of a light beam) of the illumination light L, which has exited from the light source 31, is designated as the Z-axis direction and two directions orthogonal to each other within a plane are designated as the X-axis direction and the Y-axis direction. Also, the illumination light L, which has exited from the light source 31, is schematically shown by the broken line in FIG. 2.

For example, the light source 31 radiates visible light such as white light or light in a wavelength range in the vicinity thereof as the illumination light L. In the light source 31, natural light and light from an external light source such as a white fluorescent lamp or a white light bulb can be used as the illumination light L using a reflecting mirror or the like. Also, in the light source 31, light from an internal light source such as a halogen lamp or a tungsten lamp can be used as the illumination light L.

Also, a light emitting diode (LED) or the like may be used as the light source 31. In this case, for example, the light source 31 can include a combination of LEDs that emit light of wavelengths of red, blue, and green. Also, because the wavelength of the illumination light emitted by the light source 31 can be variably controlled by controlling turning ON and OFF of LEDs having different wavelengths, it is possible to omit a wavelength conversion member such as a wavelength filter when such LEDs are used for the light source 31.

In the illumination optical system 32, a first condenser lens 37, a first spatial light modulation element 38, and a second condenser lens 39 are disposed sequentially from the light source 31 side. Among these, the first condenser lens 37 and the second condenser lens 39 radiate the illumination light L, which has exited from the light source 31, to the subject S on the stage 36.

The first spatial light modulation element 38 is disposed at a position conjugate with a pupil position of the image forming optical system 33 (an objective lens 40). The first spatial light modulation element 38 variably adjusts a light intensity distribution of the illumination light L applied to the subject S (an aperture) and it is possible to freely change a shape, a size, and the like of an opening (a region through which the illumination light L passes) 38a of the aperture.

In the image forming optical system 33, the objective lens 40 and the second spatial light modulation element 41 are disposed sequentially from the above-described stage 36 side.

The objective lens 40 causes an image of the transmitted light Lp from the subject S to be formed on a light receiving surface of the solid-state imaging element 34.

The second spatial light modulation element 41 is disposed at or near the pupil position of the objective lens 40. Also, the first spatial light modulation element 38 and the second spatial light modulation element 41 are disposed at positions conjugate with each other.

The second spatial light modulation element 41 variably adjusts a spatial distribution of phases added to the transmitted light Lp from the subject S and adjusts the phase added to the transmitted light Lp to 0° or ±90°. Specifically, the second spatial light modulation element 41 includes a phase modulation region 41a that causes direct light ($0^{th}$-order light), which has passed through the subject S within the transmitted light Lp from the subject S, to pass in a state in which the phase of the direct light has been shifted by a quarter wavelength (±90°) and a diffracted light transmission region 41b where diffracted light diffracted by the subject S around the phase modulation region 41a is allowed to pass at the phase (0°) as it is.

The second spatial light modulation element 41 can freely change a shape, a size, and the like of the phase modulation region 41a with respect to the diffracted light transmission region 41b. Also, for example, a liquid crystal panel (a liquid crystal element) or the like can be used as the above-described second spatial light modulation element 41.

Further, it is preferable that the second spatial light modulation element 41 have a function of variably adjusting a spatial distribution of transmittance at which the transmitted light Lp from the subject S is transmitted together with the above-described spatial distribution of phases. In general, because the direct light transmitted through the phase modulation region 41a within the transmitted light Lp passing through the second spatial light modulation element 41 has a higher light intensity than the diffracted light transmitted through the diffracted light transmission region 41b, adjustment for weakening a light intensity is performed using a neutral diffraction (ND) filter or the like.

For example, the solid-state imaging element 34 includes a plurality of light receiving elements having different light receiving wavelengths such as a charge-coupled device (CCD) image sensor and a complementary metal-oxide-semiconductor (CMOS) image sensor. The solid-state imaging element 34 receives the transmitted light Lp whose image is formed by the above-described image forming optical system 33, converts the received transmitted light Lp into an electrical signal (an image signal), and outputs the electrical signal (the image signal) to the determination device 100.

In the phase-contrast microscope having the above-described structure, the illumination light L, which has exited from the light source 31, passes through the first condenser lens 37 and is incident on the first spatial light modulation element 38. The illumination light L that has passed through the opening 38a of the first spatial light modulation element 38 passes through the second condenser lens 39 and is radiated to the subject S placed on the placement surface 36a of the stage 36.

After the transmitted light Lp from the subject S passes through the objective lens 40, the transmitted light Lp is incident on the second spatial light modulation element 41. At this time, in a state in which a phase of the direct light transmitted through the phase modulation region 41a within the transmitted light Lp from the subject S is shifted by a quarter wavelength, an image of the direct light is formed on the light receiving surface of the solid-state imaging element 34 after the light is dimmed by the ND filter. On the other hand, an image of the diffracted light transmitted through the diffracted light transmission region 41b is imaged on the light receiving surface of the solid-state imaging element 34 at the phase (0°) as it is. In the phase-contrast microscope, it is possible to observe the change in phase as contrast of light due to the interference between the straight light and the diffracted light.

<Regarding Determination Target Cells>

A specific example of the subject S observed by the microscope 30, i.e., a determination target cell of the determination system 1, will be described. An example of the subject S is a cell containing melanin granules and is, for example, a cell (a type of cell) having a color tone such as a visual cell, a retinal pigment epithelium (RPE) cell a skin cell, a melanocyte, or a red blood cell (having hemoglobin which is one type of red blood cytoplasm). For example, a type of cell, which exhibits such a color tone, may make a change in the color tone in a differentiation induction and maturation process from a stem cell to a target somatic cell.

Specifically, the color of the visual cell or the RPE cell is light "immediately after seeding" or "immediately after differentiation induction" and the number of pigment-positive cells increases and the color becomes darker with the passage of time. That is, the color tone of the visual cell or the RPE cell changes from red to brown in the differentiation induction and maturation process.

The determination device 100 according to the present embodiment determines a cultured state of whether or not the growth has progressed normally or the like by determining which of growth processes corresponds to the subject S or the like on the basis of the color information of the subject S. According to this configuration, the determination device 100 according to the present embodiment can determine whether or not the differentiation induction and maturation of the subject S have progressed normally for a culture period. The description will be continued with reference again to FIG. 1.

<Configuration of Determination Device>

Next, a configuration of the determination device 100 will be described. The determination device 100 includes a control unit 102 and a storage unit 112.

The storage unit 112 includes a hard disk, a non-volatile storage medium such as a flash memory, and a volatile storage medium such as a dynamic random access memory (DRAM) or a static random access memory (SRAM). The storage unit 112 pre-stores a program 114 that causes the control unit 102 to execute a process of determining whether or not cell growth has progressed normally, image information 116, and color reference information 120.

The image information 116 is image information of an enlarged image of the subject S acquired by the control unit 102. For example, as an example of a sample cell, the visual cell or the RPE cell changes to a light color, a red color, and a brownish-red color as the growth process progresses to differentiation induction or maturation from the time "immediately after seeding" or "immediately after differentiation induction." Here, color information of the sample cell will be described.

<Color Information (Part 1)>

Figure 3:
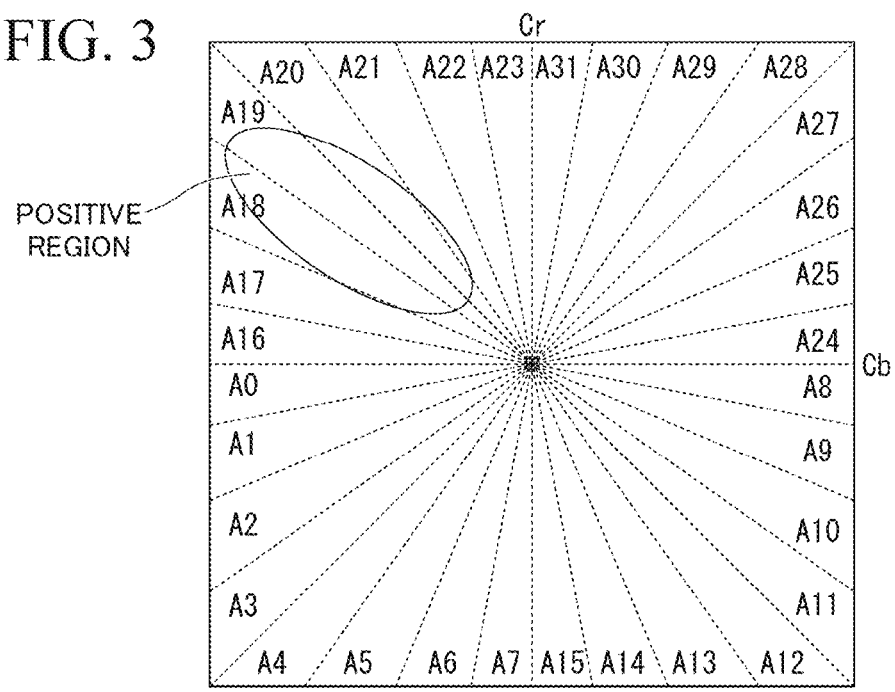
FIG. 3 is a diagram showing an example of a color space (part 1).

FIG. 3 shows a color space expressed by a hue vector (CbCr) obtained by excluding a luminance signal Y from a color space expressed by YCbCr. In FIG. 3, a color region (a positive region) where sample cells change as growth progresses to the differentiation induction process or the cell maturation process from the time "immediately after seeding" or "immediately ater differentiation induction" is shown.

<Color Information (Part 2)>

Figure 4:
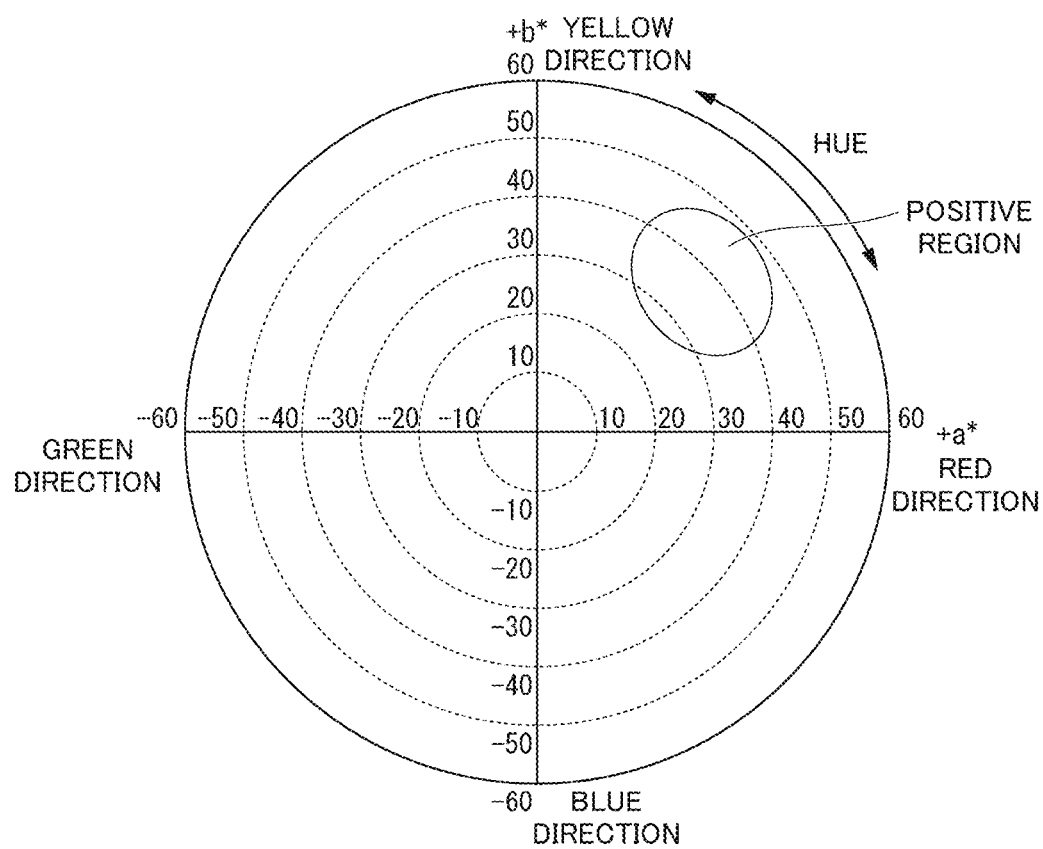
FIG. 4 is a diagram showing an example of a color space (part 2).

FIG. 4 shows a color space expressed by chromaticity (a*, b*) representing hue and saturation in a state in which L* representing brightness is excluded from an L*a*b* color space. In FIG. 4, as in FIG. 3, a color region (a positive region) where the sample cell changes as growth progresses to the differentiation induction process or the cell maturation process from the time "immediately after seeding" or "immediately after differentiation induction" is shown.

<Color Information (Part 3)>

A color range may be represented by hue within an HSV color space including three components of hue (Hue), saturation (Saturation/Chroma), and brightness (Value/Lightness/Brightness).

The color information of the subject S may be determined by any one of <color information (part 1)> to <color information (part 3)> or the color information of the subject S may be determined by a combination of at least two of <color information (part 1)> to <color information (part 3)>. Here, three methods of <color information (part 1)> to <color information (part 3)> are examples and the color information of the subject S may be determined in a method other than the above.

Examples of the color information include information about hue, information about saturation, information about brightness, information about luminance, information about a color difference, and the like, but the color information may be a combination thereof and is not limited thereto.

Also, for example, the color information of the subject S may be determined on the basis of at least one of the information about hue, the information about saturation, the information about brightness, the information about luminance, and the information about a color difference and is not limited thereto.

The description will be continued with reference again to FIG. 1. The color reference information 120 stores color information in one or more growth processes of the sample cells. Here, the color reference information 120 is color information of the sample cells when a predetermined time period has elapsed from the time "immediately after seeding" or "immediately after differentiation induction" and is color information of the sample cell that change with the progress of growth to a differentiation induction process or a cell maturation process. The color information included in the color reference information 120 includes information about a positive region. In the color reference information 120, for example, the elapsed time period from the time "immediately after seeding" or "immediately after differentiation induction" and the color information for the elapsed time period are stored in association.

Further, information representing a positive range set on the basis of a result of plotting the color information obtained by analyzing color information regarding Cb and color information regarding Cr in an image of each of one or more cells included in sample cells in a certain growth process in a color space represented by Cb and Cr is stored in the color reference information 120.

<Method of Setting Color Reference Information 120>

Figure 5:
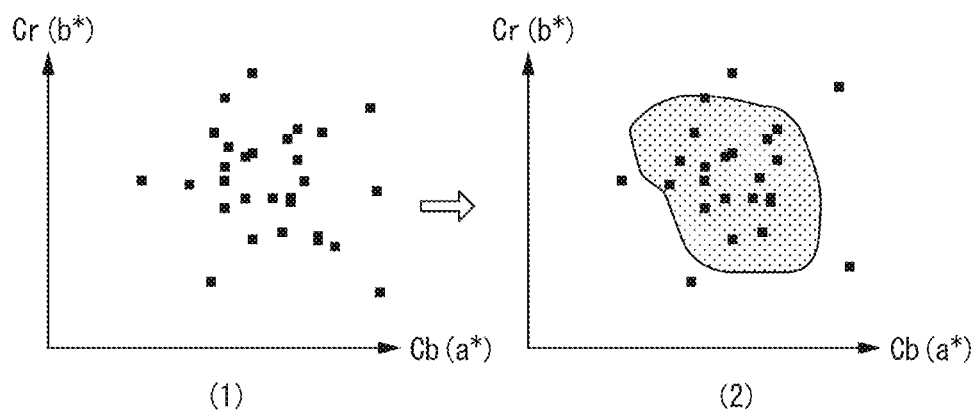
FIG. 5 is a diagram showing a method (pan 1) of setting color reference information (part 1).

FIG. 5 shows a setting method (part 1) of the color reference information 120. FIG. 5(1) shows a result of analyzing color information of an image of sample cells in a certain growth process and plotting color information in a color space expressed by Cb and Cr Here, the growth process represents that the sample cells change to a differentiation induction process or a cell maturation process from the time "immediately after seeding" or "immediately after differentiation induction." For example, the color information regarding Cb and the color information regarding Cr in an image of each of one or more cells included in the sample cells in a certain growth process are analyzed and the analyzed color information is plotted in the color space expressed by Cb and Cr.

FIG. 5(2) shows an example in which a positive region is set on the basis of the color information plotted in the color space expressed by Cb and Cr on the basis of FIG. 5(1). For example, the positive region is set by a range of Cb and a range of Cr so that about 80% of the color information plotted as shown in FIG. 5(1) is covered. In FIG. 5(2), the positive region is shaded. Here, 80% of the plotted color information covered by the positive region is an example and a proportion of the plotted color information covered by the positive region may be less than 80% or greater than 80%.

Although a case in which the color information of the image of sample cells in a certain growth process is plotted in the color space expressed by Cb and Cr is shown in FIGS. 5(1) and 5(2), the present invention is not limited thereto. For example, the present invention can also be applied to a case in which the color information of an image of sample cells in a certain growth process is plotted in a color space expressed by chromaticity (a*, b*) representing hue and saturation in a state in which L* representing brightness has been excluded from the L*a*b* color space described with reference to FIG. 4.

Figure 6:
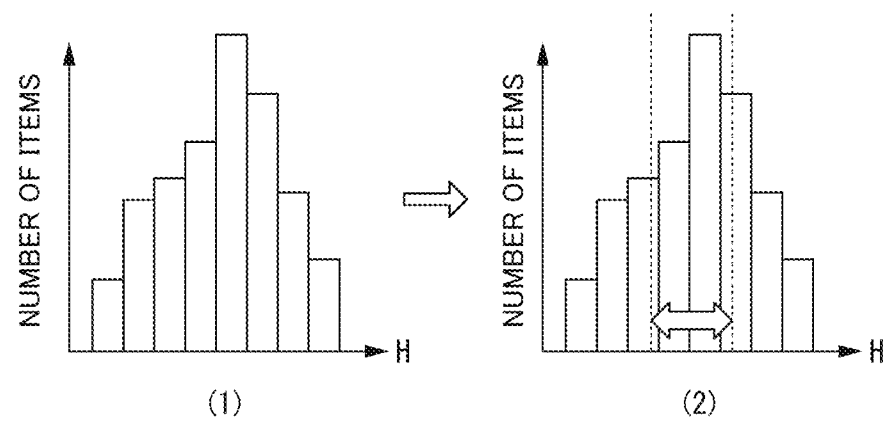
FIG. 6 is a diagram showing a method (part 2) of setting color reference information.

FIG. 6 shows a method (part 2) of setting the color reference information 120. FIG. 6(1) shows a result of obtaining hue (H) by analyzing the color information of the image of sample cells in a certain growth process and obtaining a distribution of the hue (H) by plotting the hue (H). In FIG. 6(1), the X-axis represents the hue (H). For example, color information of an image of each of one or more cells included in the sample cells in the certain growth process is analyzed and hue (H) of the image of each of the one or more cells is plotted.

FIG. 6(2) shows an example in which a positive range is set on the basis of the distribution of the hue (H) shown in FIG. 6(1). For example, in the distribution of the hue (H) shown in FIG. 6(1), the positive range is set according to a range of the hue (H) so that about 80% of the distribution is covered. Here, 80% which is a proportion of the hue plotted to be covered by the positive region is an example and the proportion of the hue plotted to be covered by the positive region may be less than 80% or greater than 80%.

The control unit 102 is implemented by, for example, a central processing unit (CPU), and executes the program 114 stored in the storage unit 112, so that the control unit 102 functions as an image acquisition unit 104, an image processing unit 106, a color information conversion unit 108, and a determination unit 110.

The image acquisition unit 104 acquires an image of the subject S provided by the microscope 300 and stores the image in the image information 116 of the storage unit 112. For example, the image acquisition unit 104 periodically acquires the image of the subject S provided by the microscope 300 and stores image information of the subject S in the image information 116 of the storage unit 112. The image acquisition unit 104 may be configured to store information representing the elapsed time period from the time "immediately after seeding" or "immediately after differentiation induction" together with the image information of the subject S in the storage unit 112.

The image processing unit 106 acquires the image information of the subject S stored in the image information 116 of the storage unit 112 and executes image processing on the acquired image information of the subject S. An example of the image processing is color correction, color conversion, color adjustment, color tone adjustment "edge detection" for finding a boundary from a change in a concentration, or the like. For example, the image processing unit 106 performs image processing on the image information of the subject S acquired from the image information 116 of the storage unit 112.

The image processing unit 106 extracts a target for measuring the color information of the image obtained by performing the image processing. Specifically, the image processing unit 106 extracts one or more cells such as one or more cell clusters or one or more paving stone-shaped cells as a target for measuring color information from the image obtained by performing the image processing. The image processing unit 106 outputs image information of the one or more cells that have been extracted to the color information conversion unit 108.

Figure 7:
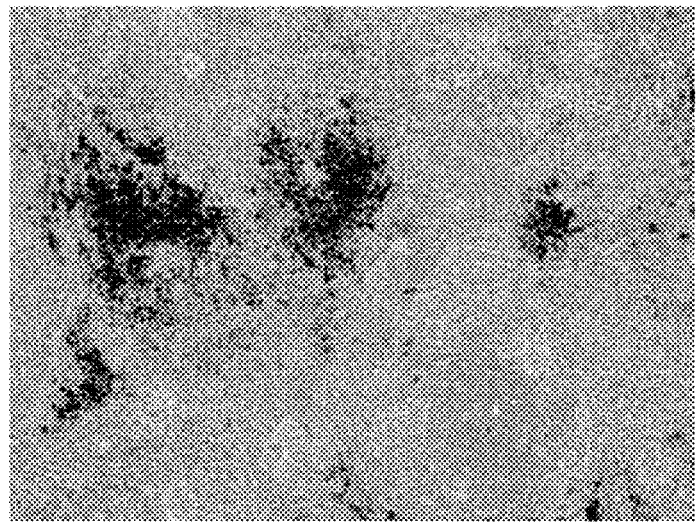
FIG. 7 is a diagram showing an example of a process of extracting a target for measuring color information.
Figure 7:
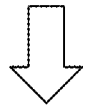
Figure 7:
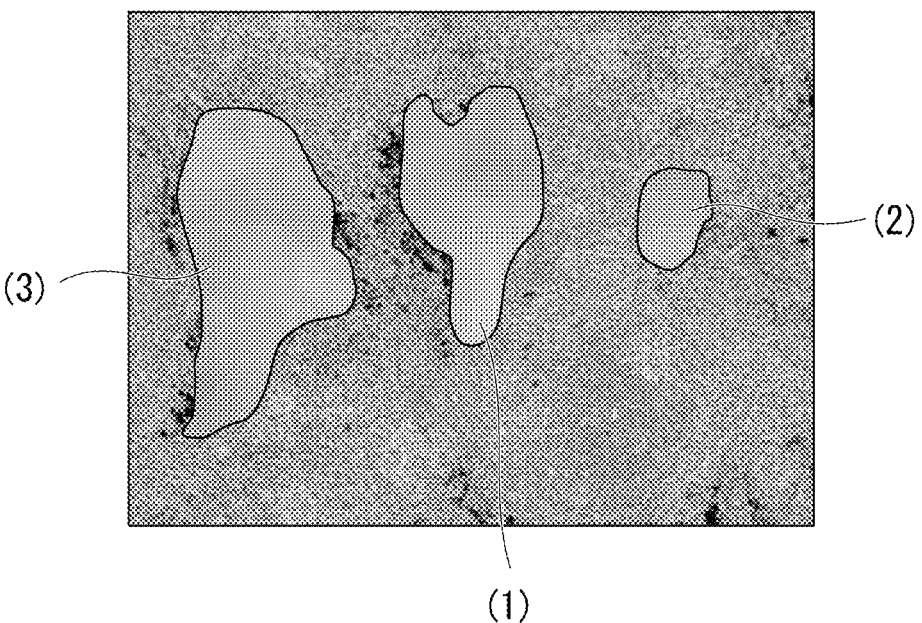

FIG. 7 shows an example of a process of obtaining one or more cells as a target for measuring color information from an image of RPE cells during differentiation induction. The image processing unit 106 executes image processing on image information of a subject S and extracts a plurality of cell clusters (1) to (3) as a target for measuring color information from the image obtained by the image processing.

Figure 8:
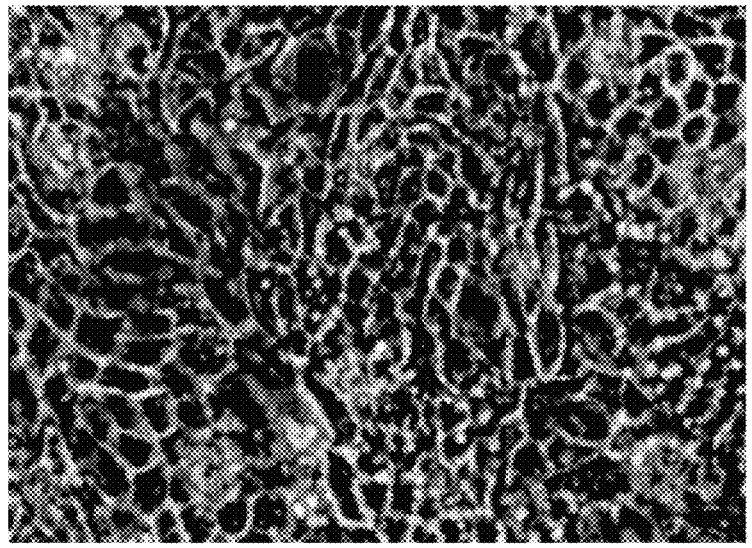
FIG. 8 is a diagram showing an example of a process of extracting a target for measuring color information.
Figure 8:
Figure 8:
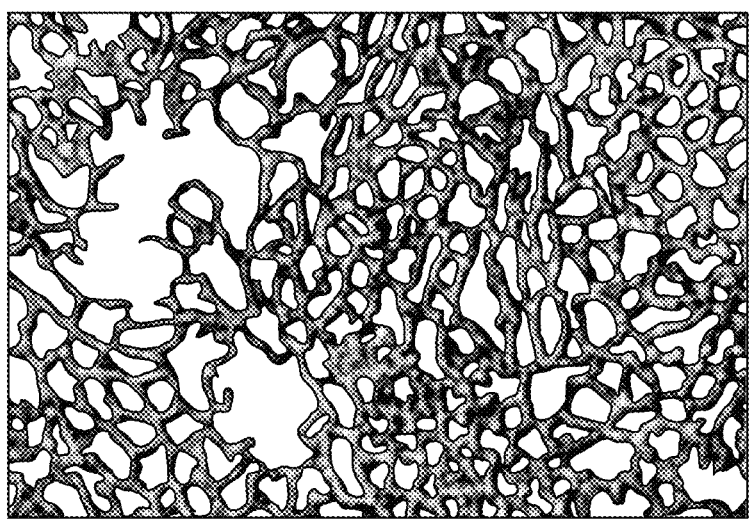

FIG. 8 shows an example of a process of extracting one or more cells as a target for measuring color information from an image of RPE cells in the maturation process. In the example shown in FIG. 8, the image processing unit 106 executes image processing on image information of a subject S and extracts a plurality of paving stone-shaped cells as a target for measuring color information from an image obtained through the image processing.

The description will be continued with reference again to FIG. 1. The color information conversion unit 108 measures a color of an image obtained by image information of one or more cells supplied by the image processing unit 106. The color information conversion unit 108 acquires information representing a positive range from the color reference information 120 of the storage unit 112 and obtains a proportion (hereinafter referred to as a "positive rate") of color information included in a positive region within the color information of the image of the one or more cells on the basis of the acquired information representing the positive range.

Hereinafter, as an example, a case in which the color information conversion unit 108 uses a color space expressed by Cb and Cr as color information will be described with reference to FIG. 9.

Figure 9:
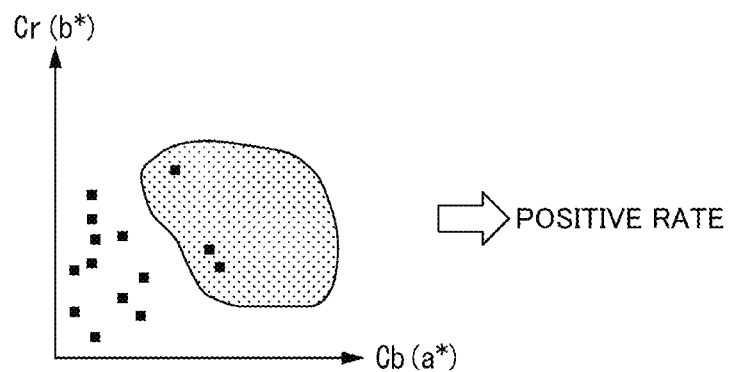
FIG. 9 is a diagram showing an example (part 1) of analysis of color information.

FIG. 9 shows a result of analyzing the color information of an image of one or more cells and plotting the color information in the color space expressed by Cb and Cr. For example, the color information conversion unit 108 analyzes the color information of the image of the one or more cells and plots the color information of the image of the one or more cells. The color information conversion unit 108 acquires information representing a positive range from the color reference information 120 of the storage unit 112 and obtains a positive rate on the basis of the acquired information representing the positive range. The hatching in FIG. 9 is a positive region obtained on the basis of the information representing the positive range acquired from the color reference information 120 of the storage unit 112. This positive region is the same as the positive region shown in FIG. 5.

The color information conversion unit 108 obtains a positive rate on the basis of color information of a plotted image of one or more cells. For example, the color information conversion unit 108 obtains the positive rate by obtaining a proportion of plots included in the positive region among all plots of the color information of the image of the one or more cells. The color information conversion unit 108 outputs information representing the positive rate to the determination unit 110.

Hereinafter, as another example, a case in which the color information conversion unit 108 uses a hue distribution as the color information will be described with reference to FIG. 10.

Figure 10:
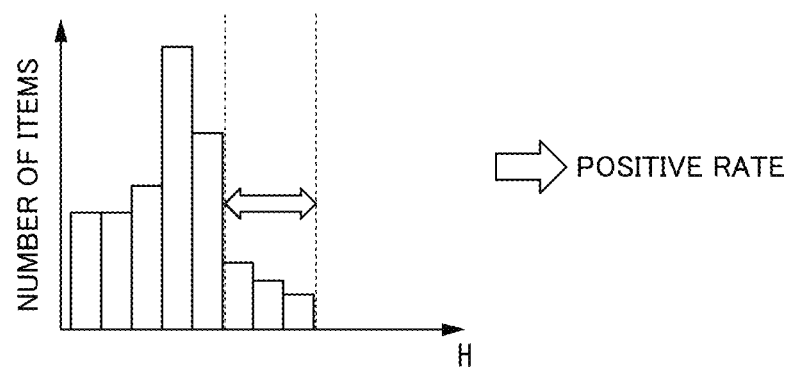
FIG. 10 is a diagram showing an example (part 2) of analysis of color information.

FIG. 10 shows a result of obtaining hue (H) by analyzing color information of an image of one or more cells and obtaining a distribution (a histogram) of the hue (H) as a distribution of the color information by plotting the hue (H). For example, the color information conversion unit 108 analyzes the color information of the image of the one or more cells and plots the hue (H) of the image of the one or more cells. The color information conversion unit 108 acquires information representing a positive range from the color reference information 120 of the storage unit 112. The range indicated by the arrow in FIG. 10 represents the positive range.

The color information conversion unit 108 obtains a positive rate on the basis of the plotted hue (H) of the image of the one or more cells and the information representing the positive range acquired from the color reference information 120 of the storage unit 112. For example, the color information conversion unit 108 obtains the positive rate by obtaining a proportion of plots included in the positive range among all plots of the hue (H) of the image of the one or more cells. The color information conversion unit 108 outputs information representing the positive rate to the determination unit 110.

The description will be continued with reference again to FIG. 1. The determination unit 110 determines whether or not the subject S has grown normally on the basis of the information representing the positive rate supplied by the color information conversion unit 108. For example, the determination unit 110 determines that the subject S has grown normally when a value of the positive rate which is supplied periodically has gradually increased and determines that the subject S has not grown normally when a value of the positive rate has not gradually increased. The determination unit 110 outputs information representing a result of determining whether or not the subject S has grown normally to the display device 200.

The display device 200 is implemented by a liquid crystal display, a plasma display, an organic EL display, or the like and displays the result of determining whether or not the subject S has grown normally supplied by the determination unit 110 of the determination device 100.

<Operation of Determination Device>

Figure 11:
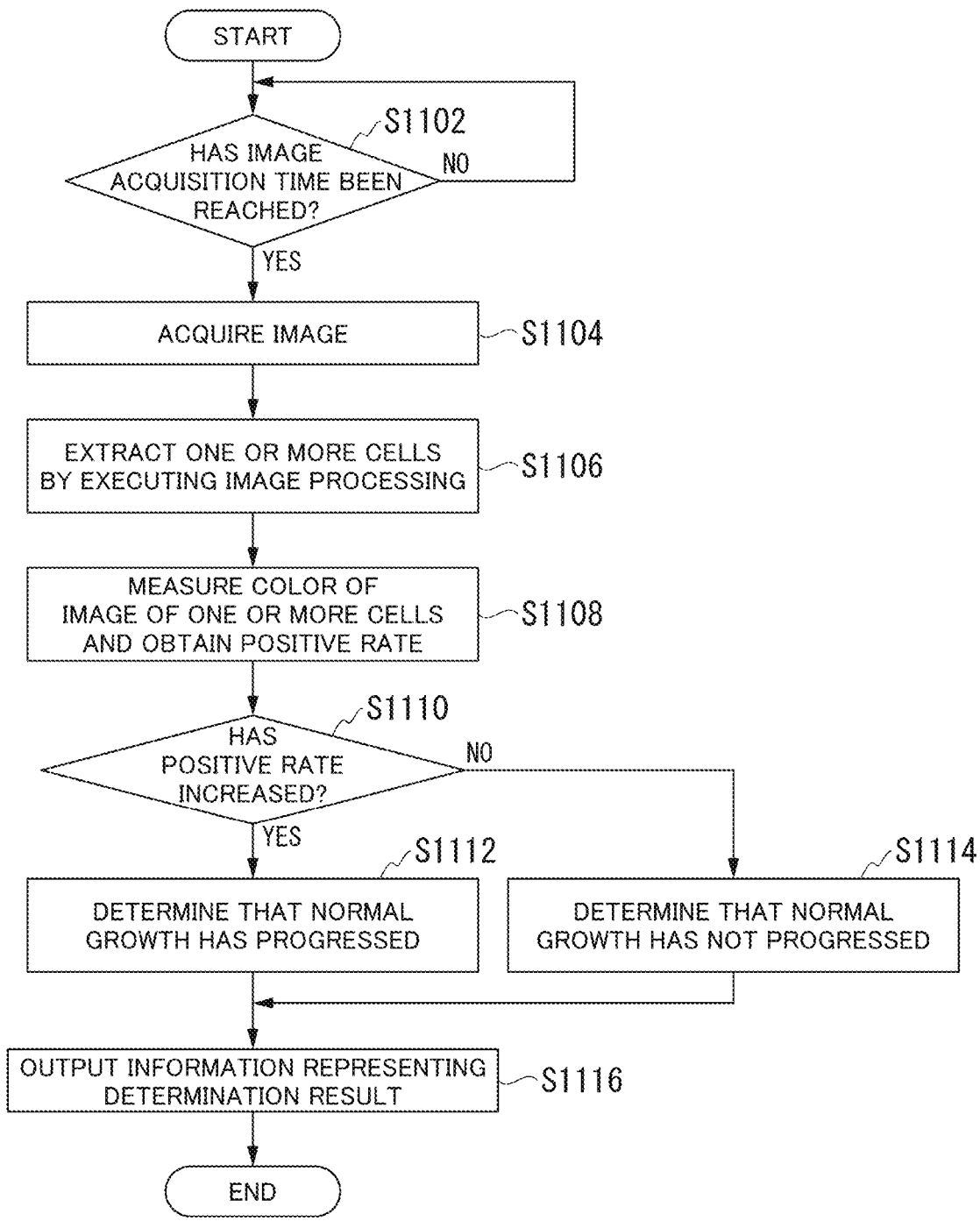
FIG. 11 is a flowchart showing an operation of a determination device according to the present embodiment.

An operation of the determination device 100 according to the present embodiment will be described with reference to FIGS. 11 and 12. FIG. 11 shows an example of the operation of the determination device 100 according to the present embodiment. A case in which the determination device 100 periodically acquires an image will be described with reference to FIG. 11. However, the present invention is not limited to the above example and can also be applied to a case in which the determination device 100 non-periodically acquires an image.

In step S1102, the image acquisition unit 104 determines whether or not an image acquisition time has been reached. When the image acquisition time has not been reached, the image acquisition unit 104 waits for the image acquisition time to be reached.

In step S1104, the image acquisition unit 104 acquires an image from the microscope 300 when the image acquisition time has been reached. FIG. 12(1) shows an example of an image acquired by the image acquisition unit 104. For example, the image acquisition unit 104 stores image information of the acquired image in the image information 116 of the storage unit 112.

Figure 13:
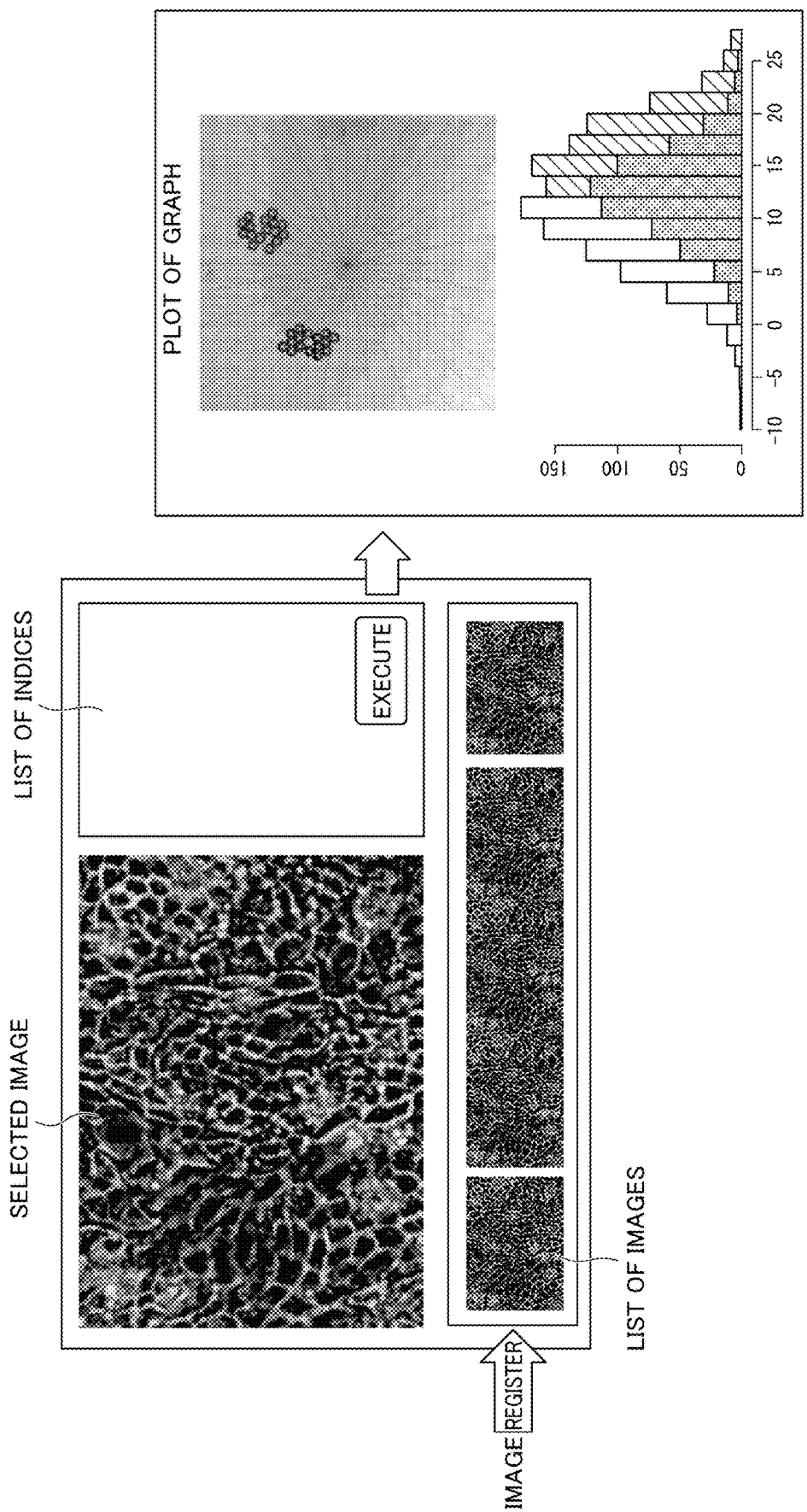
FIG. 13 is a diagram showing an example of a graphical user interface of the determination device according to the present embodiment.

FIG. 13 is a diagram showing an example of a graphical user interface (GUI) of the determination device 100 according to the present embodiment. This GUI is displayed on the display device 200 connected to the determination device 100. In the example shown in FIG. 13, the GUI includes a region where a list of images is displayed, a region where a selected image is displayed, and a region where a list of indices is displayed. In the region where the list of images is displayed, thumbnails of images included in the image information 116 of the storage unit 112 are displayed. In the region where the selected image is displayed, one or more images selected by the user of the determination device 100 from the thumbnails of one or more images displayed in the region where the list of images is displayed are displayed. In the region where the list of indices is displayed, indexes capable of being derived from one or more images are displayed. The description will be continued with reference again to FIG. 11.

In step S1106, the image processing unit 106 processes the image information of the image acquired by the image acquisition unit 104 and extracts one or more cells such as cell clusters or paving stone-shaped cells to extract a color measurement target. FIG. 12(2) shows an example of a paving stone-shaped image extracted by performing image processing in the image processing unit 106. In the image, a region serving as a color measurement target and a region other than the color measurement region are displayed separately. The description will be continued with reference again to FIG. 11.

In step S1108, the color information conversion unit 108 measures a color of an image of one or more cells extracted by the image processing unit 106.

Figure 14:
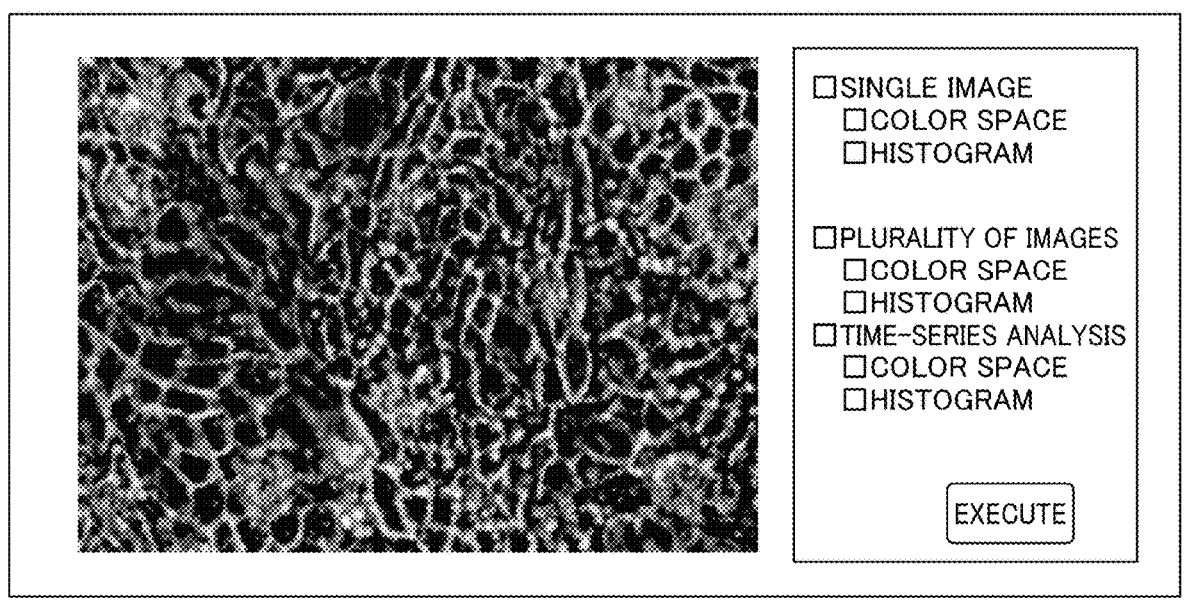
FIG. 14 is a diagram showing an example of a graphical user interface of the determination device according to the present embodiment.

FIG. 14 is a partial view showing an example of the graphical user interface of the determination device 100. In FIG. 14, a region where the selected image is displayed and a region where the list of indices is displayed in the graphical user interface shown in FIG. 13 are shown. In the example shown in FIG. 14, a color space and a histogram are shown as an example of an index capable of being derived from a single image. Also, as an example of an index capable of being derived from a plurality of images, a color space and a histogram are shown. Also, a color space and a histogram are shown as an example of an index capable of being derived from time-series analysis. Further, in the example shown in FIG. 14, check boxes for selecting each index are shown.

The user of the determination device 100 causes a check mark to be displayed in the check box corresponding to the index to be displayed in the GUI shown in FIG. 14. For example, when the user of the determination device 100 causes a check mark to be displayed in the check box of a plurality of images, the check box of a color space, and the check box of a histogram and has pressed an execute button, a graph showing the color information of a plurality of images in a color space and a graph showing the color information of a plurality of images in a histogram are displayed as shown in a plot of a graph of the lower-right portion of FIG. 13.

The color information conversion unit 108 acquires information representing a positive range from the color reference information 120 of the storage unit 112 and determines whether or not a value obtained by measuring a color of one or more cells is included in the positive region on the basis of the acquired information representing the position range. The color information conversion unit 108 determines a positive rate on the basis of a result of determining whether or not the value obtained by measuring the color of the one or more cells is included in the positive region.

Here, the color information conversion unit 108 may be configured to output information representing information of a paving stone-shaped image in which a positive region and a region which is not included in the positive region among regions serving as color measurement targets and a region other than the regions serving as the color measurement targets are distinguished to the display device 200. In this case, as shown in the left drawing of FIG. 12(3), the display device 200 separately displays a positive region and a region which is not included in the positive region among regions serving as color measurement targets and a region other than the regions serving as the color measurement targets.

Further, the color information conversion unit 108 may be configured to output information representing the number of cells included in the positive region and the number of cells included in the region which is not included in the positive region in the number of cells included in the regions serving as the color measurement targets and the number of cells included in the region other than the regions serving as the color measurement targets to the display device 200.

Figure 12:
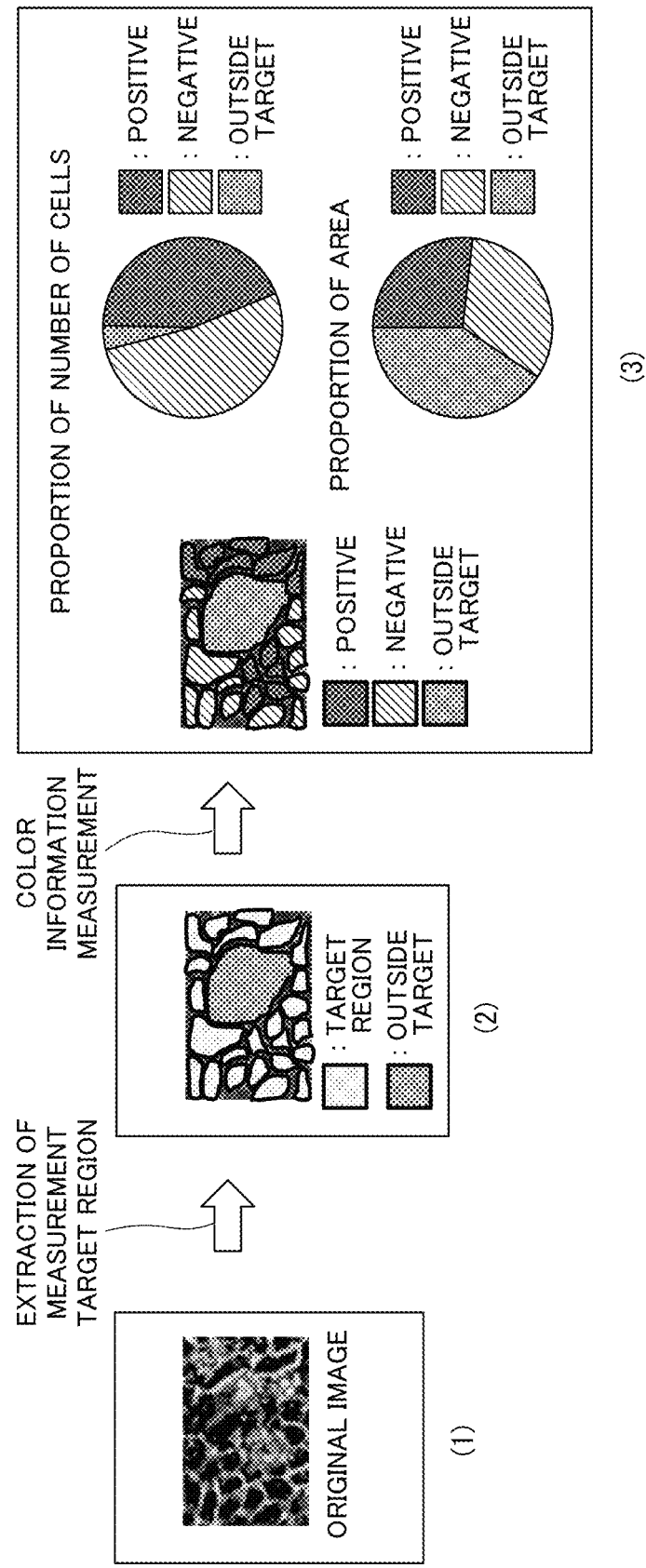
FIG. 12 is a diagram showing an operation of the determination device according to the present embodiment.

In this case, as shown in the upper-right portion of FIG. 12(3), the display device 200 separately displays the number of cells included in the positive region and the number of cells included in the region which is not included in the positive region in the number of cells included in the regions serving as the color measurement targets and the number of cells included in the region other than the regions serving as the color measurement targets.

Further, the color information conversion unit 108 may be configured to output information representing an area of the positive region and an area which is not included in the positive region among areas of regions serving as the color measurement targets and an area of the region other than the regions serving as the color measurement targets to the display device 200.

In this case, as shown in the lower-right portion of FIG. 12(3), the display device 200 separately displays the area of the positive region and the area which is not included in the positive region among the areas of the regions serving as the color measurement targets and the area of the region other than the regions serving as the color measurement targets. The description will be continued with reference again to FIG. 11.

In step S1110, the determination unit 110 determines whether or not the positive rate has increased as compared with a previously supplied positive rate. Here, when the positive rate has been initially supplied, the determination unit 110 retains the positive rate and returns to step S1102.

In step S1112, the determination unit 110 determines that the growth has progressed normally when the positive rate has increased.

In step S1114, the determination unit 110 determines that the growth has not progressed when the positive rate has not increased.

In step S1116, the determination unit 110 outputs information representing a determination result in step S1112 or information representing a determination result in step S1114. For example, when the information representing the determination result has been output to the display device 20, the display device 200 displays the determination result.

Although an example in which the color information in one or more growth processes of the sample cells and the information representing the positive range included in the color reference information 120 are pre-stored in the determination device 100 has been described in the above-described embodiment, the present invention is not limited to this example.

For example, the color information in one or more growth processes of the sample cells and the information representing the positive range included in the color reference information 120 may be accumulated or updated on the basis of a result of measuring a color of an image obtained according to image information of one or more cells in the color information conversion unit 108. According to this configuration, it is possible to accumulate or update the color information in the growth process and the information representing the positive range on the basis of the color measurement result. In this case, an accumulating process and an updating process may be executed by the control unit 102.

According to this configuration, the determination device according to the present embodiment can perform a process without the color information in one or more growth processes of the sample cells and the information representing the positive range included in the color reference information 120 having been previously provided.

Also, in the above-described embodiment, when the color information conversion unit 108 may analyze color information of an image of each of one or more cells, the color information may be analyzed for each pixel. According to this configuration, the determination device according to the present embodiment can perform analysis in a short time from the step before the form of one or more cells becomes clear.

The determination device according to the present embodiment acquires an enlarged image of the subject S and extracts one or more cells such as one or more cell clusters or paving stone-shaped cells included in the subject S. The determination device determines whether or not the growth has progressed normally on the basis of whether or not a proportion of cells included in a positive region assumed to change as cell growth progresses has increased on the basis of color information of an image of each of one or more cells.

When growth has progressed normally, it is assumed that a proportion of cells included in the positive region assumed to change as cell growth progresses increases with the passage of time from the time "immediately after seeding" or "immediately after differentiation induction." The determination device according to the present embodiment determines that the cells have grown normally when the proportion of cells included in the positive region assumed to change as cell growth progresses has increased and determines that the cells have not grown normally when the proportion has not increased. According to this configuration, the determination device according to the present embodiment can determine whether or not the cell growth is normal in a process of culturing the cells.

Second Embodiment

Figure 15:
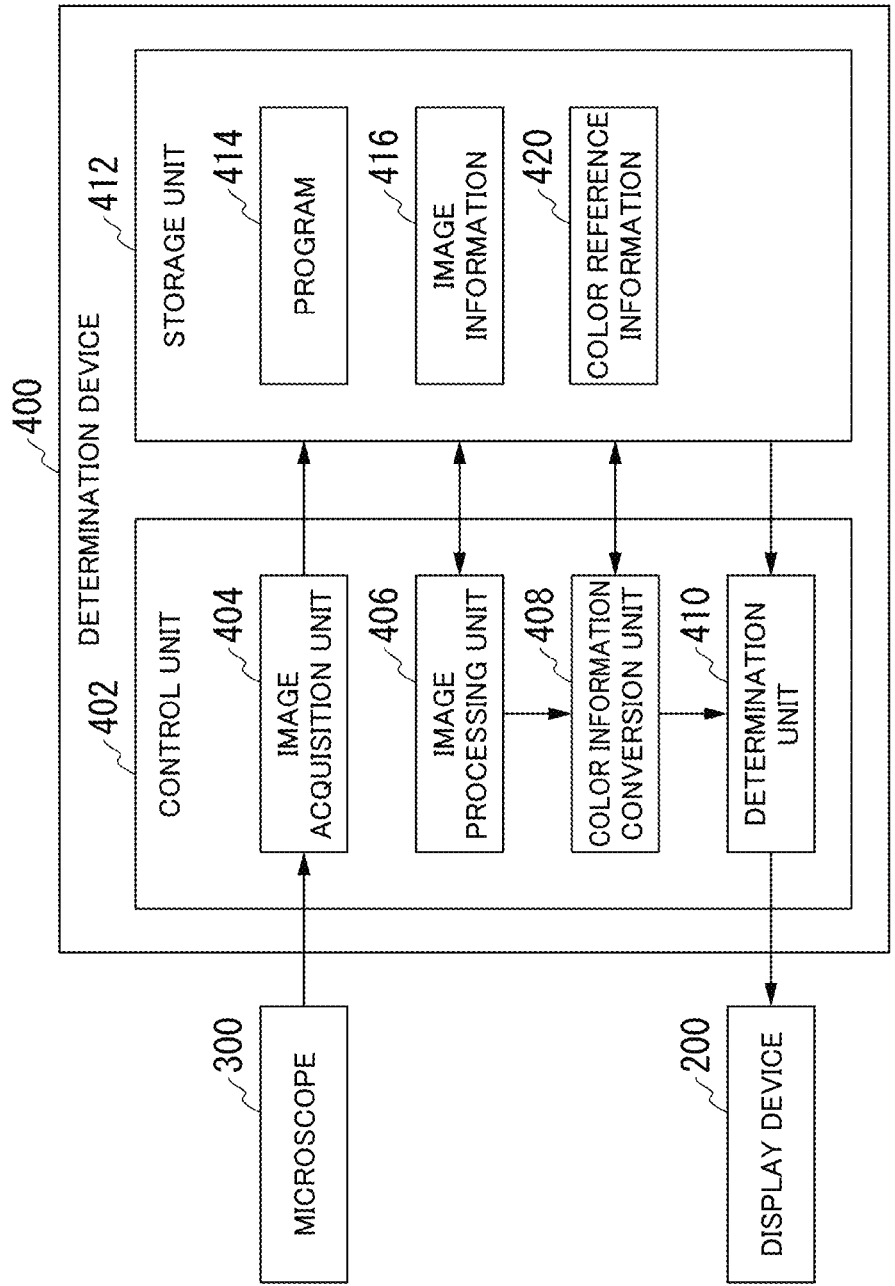
FIG. 15 is a diagram showing a determination system according to the present embodiment.

FIG. 15 shows a determination system 2 according to the present embodiment. The determination system 2 according to the present embodiment is different from the determination system 1 according to the first embodiment in a method of setting color reference information and a method of determining whether or not growth has progressed normally. The determination system 2 according to the present embodiment includes a determination device 400, a display device 200, and a microscope 300.

The determination device 400 acquires an enlarged image of a subject S provided by the microscope 300. After the enlarged image of the subject S is acquired, the determination device 400 determines whether or not the subject S has grown normally on the basis of color information of the subject S included in an image obtained by performing image processing on the enlarged image of the subject S with reference to the color information in one or more growth processes of sample cells.

Here, the color information in one or more growth processes of the sample cells is pre-stored in the determination device 400. The determination device 400 displays a result of determining whether or not the subject S has grown normally on the display device 200. According to this configuration, the determination device 400 can allow the user to know a result of evaluating whether or not the subject S has grown normally.

<Configuration of Determination Device>

Next, a configuration of the determination device 400 will be described. The determination device 400 includes a control unit 402 and a storage unit 412.

The storage unit 412 pre-stores a program 414 that causes the control unit 402 to execute a process of determining whether or not cell growth has progressed normally, image information 416, and color reference information 420.

The image information 416 is image information of an enlarged image of the subject S acquired by the control unit 402. For example, as an example of a sample cell, a visual cell or an RPE cell changes to a light color, a red color, and a brownish-red color as the growth process progresses to differentiation induction or maturation from the time "immediately after seeding" or "immediately after differentiation induction."

The color reference information 420 stores color information in one or more growth processes of sample cells. Here, the color reference information 420 is color information of sample cells when a predetermined time period has elapsed from the time "immediately after seeding" or "immediately after differentiation induction" and is color information of sample cells that change with the progress of growth to a differentiation induction process or a cell maturation process. The color information included in the color reference information 120 includes information about a positive region. In the color reference information 120, for example, the elapsed time period from the time "immediately after seeding" or "immediately after differentiation induction" and the color information for the elapsed time period are stored in association.

Further, information representing a reference value for determining a positive type set on the basis of a result of plotting color information obtained by analyzing color information regarding Cb and color information regarding Cr in an image of each of one or more cells included in sample cells in a certain growth process in a color space expressed by Cb and Cr is stored in the color reference information 420.

<Method of Setting Color Reference Information>

Figure 16:
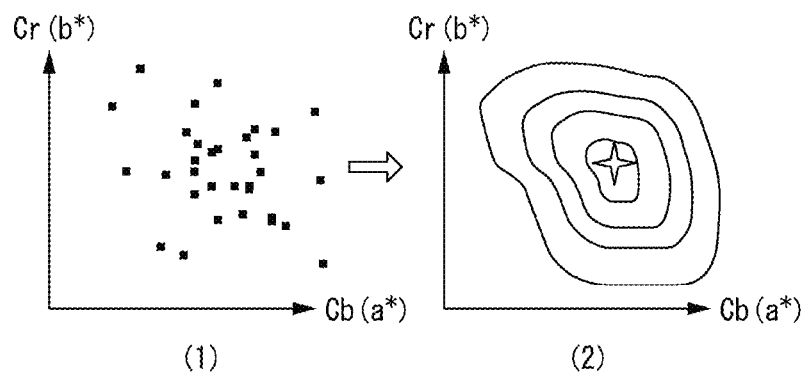
FIG. 16 is a diagram showing a method (part 3) of setting color reference information.

FIG. 16 shows a method (part 3) of setting the color reference information 420. FIG. 16(1) shows a result of analyzing color information of an image of sample cells in a certain growth process and plotting the color information in a color space expressed by Cb and Cr is shown. Here, the growth process represents that the sample cells change in a differentiation induction process or a cell maturation process from the time "immediately after seeding" or "immediately after differentiation induction." For example, color information regarding Cb and color information regarding Cr of an image of each of one or more cells included in the sample cells in a certain growth process are analyzed and the analyzed color information is plotted in the color space expressed by Cb and Cr.

FIG. 16(2) shows an example in which a reference value for determining a positive type is set on the basis of the color information plotted in the color space expressed by Cb and Cr on the basis of FIG. 16(1). For example, the center of gravity of a plurality of plots shown in FIG. 16(1) is obtained and the center of gravity are used as the reference value for determining a positive type. Here, the center of gravity is an example and statistical values such as a mean value, a median value, and a mode value may be used as the reference value for determining a positive type. Further, one or both of a standard deviation and a variance may be obtained together with the statistical values.

Although a case in which color information of an image of sample cells in a certain growth process is plotted in the color space expressed by Cb and Cr is shown in FIGS. 16(1) and 16(2), the present invention is not limited thereto. For example, the present invention can also be applied to a case in which the color information of the image of the sample cells in the certain growth process is plotted in a color space expressed by chromaticity (a*, b*) representing hue and saturation except for L* representing brightness within the L*a*b* color space described with reference to FIG. 4.

Figure 17:
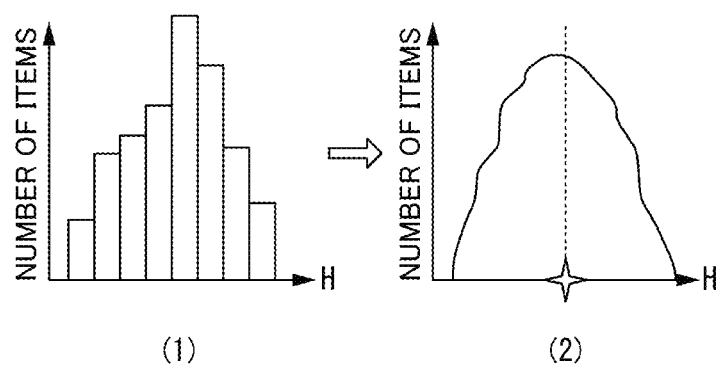
FIG. 17 is a diagram showing a method (part 4) of setting color reference information.

FIG. 17 shows a method (part 4) of setting the color reference information 420. FIG. 17(1) shows a result of obtaining hue (H) by analyzing color information of a sample image of a certain growth process and obtaining a distribution of the hue (H) by plotting the hue (H). In FIG. 17(1), the X-axis represents the hue (H). For example, color information of an image of each of one or more cells included in sample cells in a certain growth process is analyzed and hue (H) of the image of each of the one or more cells is plotted.

FIG. 17(2) shows an example in which a reference value for determining a positive type is set on the basis of the distribution of the hue (H) shown in FIG. 17(1). For example, the distribution of the hue (H) shown in FIG. 17(1) is approximated by applying the distribution of the hue (H) to a normal distribution and the center of gravity thereof is used as the reference value for determining a positive type. Here, the center of gravity is an example and statistical values such as a mean value, a median value, and a mode value can be applied. Further, the determination device 400 may obtain one or both of the standard deviation and the variance together with the statistical values.

For example, the control unit 402 is implemented by, for example, a CPU, and executes the program 414 stored in the storage unit 412, so that the control unit 402 functions as an image acquisition unit 404, an image processing unit 406, a color information conversion unit 408, and a determination unit 410.

The image acquisition unit 404 acquires an image of a subject S provided by the microscope 300 and stores the acquired image in the image information 416 of the storage unit 412. For example, the image acquisition unit 404 periodically acquires an image of the subject S provided by the microscope 300 and stores the image information of the subject S in the image information 416 of the storage unit 412. The image acquisition unit 404 may be configured to store information representing an elapsed time period from the time "immediately after seeding" or "immediately after differentiation induction" in the storage unit 412 together with the image information of the subject S.

The image processing unit 406 acquires the image information of the subject S stored in the image information 416 of the storage unit 412 and executes image processing on the acquired image information of the subject S. An example of the image processing is color correction, color conversion, color adjustment, color tone adjustment, "edge detection" for finding a boundary of a physical object from a change in a concentration, or the like. For example, the image processing unit 406 performs image processing on the image information of the subject S acquired from the image information 416 of the storage unit 412.

The image processing unit 406 extracts a target for measuring the color information from the image obtained by performing the image processing. Specifically, the image processing unit 406 extracts one or more cells such as one or more cell clusters or one or more paving stone-shaped cells as a target for measuring color information from the image obtained by performing the image processing. The image processing unit 406 outputs image information of the one or more cells that have been extracted to the color information conversion unit 408.

The color information conversion unit 408 measures a color of an image obtained by image information of each of the one or more cells supplied by the image processing unit 406. The color information conversion unit 408 obtains the center of gravity of the color information on the basis of each of one or more pieces of color information obtained by measuring a color of an image of each of the one or more cells. Here, the center of gravity of the color information is an example and the color information conversion unit 408 may obtain statistical values of the color information such as the mean value of the color information, the median value of the color information, and the mode value of the color information on the basis of each of one or more pieces of color information obtained by measuring the color of the image of each of the one or more cells. Here, the description of a case in which the center of gravity of the color information is obtained will be continued.

Further, the color information conversion unit 408 may obtain one or both of the standard deviation of the color information and the variance of the color information together with the statistical values of the color information. When one or both of the standard deviation of the color information and the variance of the color information are obtained, the color information conversion unit 408 compares one or both of the standard deviation of the color information and the variance of the color information that have been obtained with one or both of a threshold value of the standard deviation of the color information and a threshold value of the variance of the color information and outputs an alarm when the standard deviation or the variance is greater than or equal to the threshold value. The color information conversion unit 408 outputs information representing the center of gravity of the color information to the determination unit 410.

The determination unit 410 determines whether or not the subject S has grown normally on the basis of information representing the center of gravity of the color information supplied from the color information conversion unit 408. For example, the determination unit 410 acquires information representing the reference value for determining a positive type from the color reference information 420 of the storage unit 412 and calculates the distance between the center of gravity of the color information represented by the information representing the center of gravity of the color information supplied from the color information conversion unit 408 and the reference value for determining a positive type represented by the information representing the reference value for determining a positive type on the basis of the acquired information representing the reference value for determining a positive type. The determination unit 410 determines that the subject S has grown normally when the distance between the center of gravity of the color information and the reference value for determining a positive type is shorter than a previously calculated distance and determines that the subject S has not grown normally when the distance is not shorter. Here, the center of gravity of the color information is an example and may be a target for which the determination unit 410 determines statistical values of color information such as a mean value of the color information, a median value of the color information, and a mode value of the color information. The determination unit 410 outputs information representing a result of determining whether or not the subject S has grown normally to the display device 20. The description will be specifically given with reference to FIGS. 18 and 19.

Figure 18:
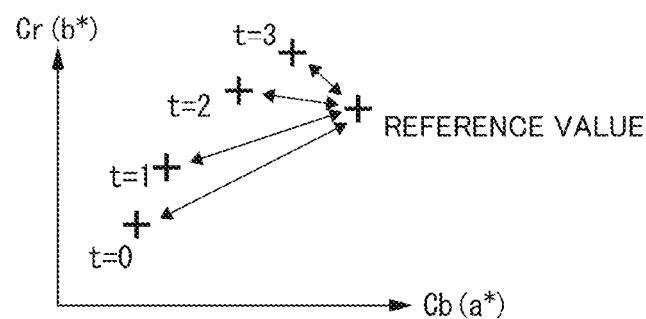
FIG. 18 is a diagram showing a process (part 1) of determining subject growth.

FIG. 18 shows a sequential change in the distance between the center of gravity of color information of an image of each of one or more sample cells obtained by plotting the color information of the image of each of the one or more sample cells in the color space expressed by Cb and Cr and a reference value for determining a positive type.

According to FIG. 18, it can be seen that the distance between the center of gravity of the color information of the image of the one or more sample cells and the reference value for determining a positive type is gradually shortened according to the passage of time (t=0, 1, 2, 3). In this case, the determination unit 410 determines that the subject S has grown normally.

Figure 19:
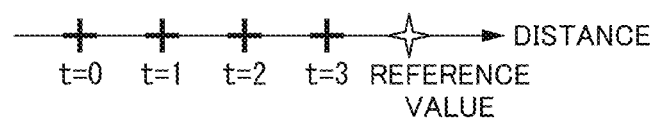
FIG. 19 is a diagram showing a process (part 2) of determining subject growth.

FIG. 19 shows a sequential change in the distance between the center of gravity of color information of an image of each of one or more sample cells and a reference value for determining a positive type. In FIG. 19, the distance between the center of gravity of the color information and the reference value for determining a positive type is shown as a relative distance from the reference value for determining a positive type.

According to FIG. 19, the distance between the center of gravity of the color information of the image of each of the one or more sample cells and the reference value for determining a positive type and the reference value for determining a positive type is close to the reference value for determining a positive type according to the passage of time (t=0, 1, 2, 3). In this case, the determination unit 410 determines that the subject S has grown normally.

<Operation of Determination Device>

Figure 20:
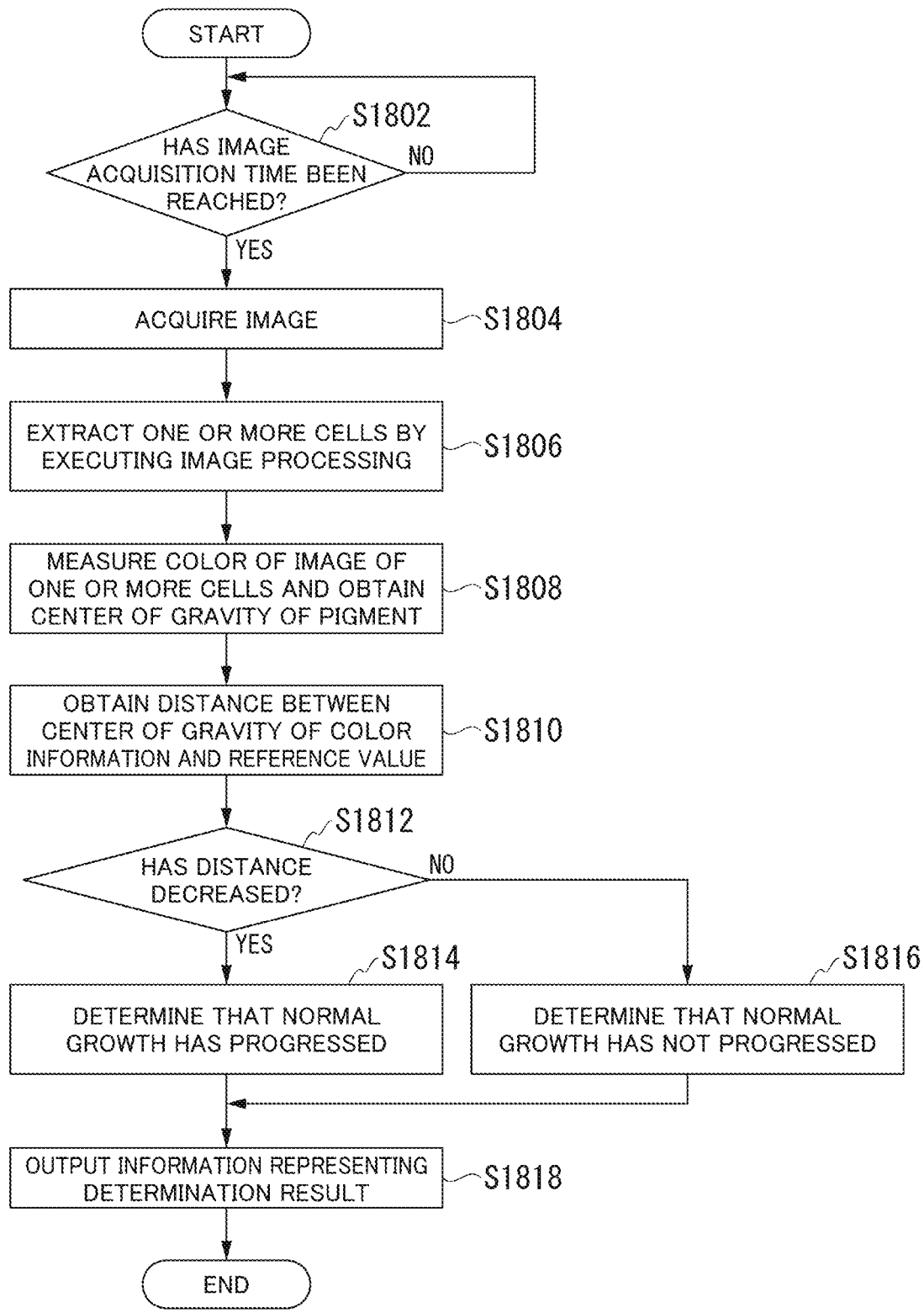
FIG. 20 is a flowchart showing an operation of the determination device according to the present embodiment.

FIG. 20 shows an example of an operation of the determination device 400 according to the present embodiment. A case in which the determination device 400 periodically acquires an image will be described with reference to FIG. 20. However, the present invention is not limited to this example and can also be applied to a case in which the determination device 400 non-periodically acquires an image.

Steps S1102 to S1106 of FIG. 11 can be applied as steps S1802 to S1806.

In step S1808, the color information conversion unit 408 measures a color of an image of each of one or more cells extracted by the image processing unit 406.

FIG. 14 can be applied for an example of the graphical user interface of the determination device 400. In the example shown in FIG. 14, a color space and a histogram are shown as an example of an index capable of being derived from a single image. Also, a color space and a histogram are shown as an example of an index capable of being derived from a plurality of images. Also, a color space and a histogram are shown as an example of an index capable of being derived from time-series analysis. Further, in the example shown in FIG. 14, a check box for selecting each index is shown.

The user of the determination device 400 causes a check mark to be displayed in the check box corresponding to the index to be displayed in the GUI shown in FIG. 14. For example, when the user of the determination device 400 causes a check mark to be displayed in a check box of a plurality of images, a check box of a color space, and a check box of a histogram and has pressed the execute button, a graph in which color information of a plurality of images is shown in a color space and a graph in which color information of a plurality of images is shown in a histogram are displayed as shown in the plot of the graph of the lower-right portion of FIG. 13.

The color information conversion unit 408 obtains the center of gravity of color information on the basis of each of one or more pieces of color information obtained by measuring a color of an image of each of one or more cells. The color information conversion unit 408 outputs information representing the center of gravity of the color information to the determination unit 410. The description will be continued with reference again to FIG. 20.

In step S1810, the determination unit 410 acquires information representing the reference value for determining a positive type from the color reference information 420 of the storage unit 412 and calculates the distance between the center of gravity of the color information represented by information representing the center of gravity of the color information supplied from the color information conversion unit 408 and the reference value for determining a positive type represented by information representing the reference value for determining a positive type on the basis of the acquired information representing the reference value for determining a positive type.

In step S1812, the determination unit 410 determines whether or not the distance between the center of gravity of the color information and the reference value for determining a positive type has been decreased.

In step S1814, the determination unit 410 determines that the growth has progressed normally when the distance between the center of gravity of the color information and the reference value for determining a positive type has been decreased.

In step S1816, the determination unit 410 determines that growth has not progressed when the distance between the center of gravity of the color information and the reference value for determining a positive type has not been decreased.

In step S1818, the determination unit 410 outputs information representing a determination result in step S1814 or information representing a determination result in step S1816. For example, when the information representing the determination result has been output to the display device 200, the display device 200 displays the determination result.

Although a case in which color information in one or more growth processes of sample cells and a reference value for determining a positive type included in the color reference information 420 are pre-stored in the determination device 400 has been described in the above-described embodiment, the present invention is not limited to this example.

For example, color information in one or more growth processes of the sample cells and information representing a positive range included in the color reference information 420 may be accumulated or updated on the basis of a result of measuring a color of an image obtained according to image information of one or more cells in the color information conversion unit 408. According to this configuration, it is possible to accumulate or update color information in the growth process and information representing a positive range on the basis of the color measurement result. In this case, an accumulating process and an updating process may be executed by the control unit 402.

According to this configuration, the determination device 400 according to the present embodiment can perform a process without color information in one or more growth processes of sample cells and information representing a positive range included in the color reference information 420 having been previously stored.

Also, in the above-described embodiment, when the color information conversion unit 408 may analyze color information of an image of each of one or more cells, the color information may be analyzed for each pixel. According to this configuration, the determination device according to the present embodiment can perform analysis in a short time from the step before the form of one or more cells becomes clear.

The determination device according to the present embodiment acquires an enlarged image of the subject S and extracts one or more cells such as one or more cell clusters or paving stone-shaped cells included in the subject S. The determination device obtains a statistical value on the basis of color information of an image of each of one or more cells and determines whether or not the growth has progressed normally on the basis of the distance between the statistical value and the reference value for determining a positive type.

When growth has progressed normally, it is assumed that, because the statistical value is close to the reference value for determining a positive type with the passage of time from the time "immediately after seeding" or "immediately after differentiation induction," the distance between the statistical value and the reference value for determining a positive type is short.

The determination device according to the present embodiment determines that cells have grown normally when the distance between the statistical value and the reference value for determining a positive type becomes short according to the progress of cell growth and determines that cell has not grown normally when the distance does not become short. According to this configuration, the determination device according to the present embodiment can determine whether or not the cell growth is normal in a process of culturing the cells.

Further, the determination device according to the present embodiment can reduce the load of a calculation process because it is unnecessary to calculate color information of an image of each of one or more cells by making a determination on the basis of a statistical value of color information of each of one or more cells.

Third Embodiment

Figure 21:
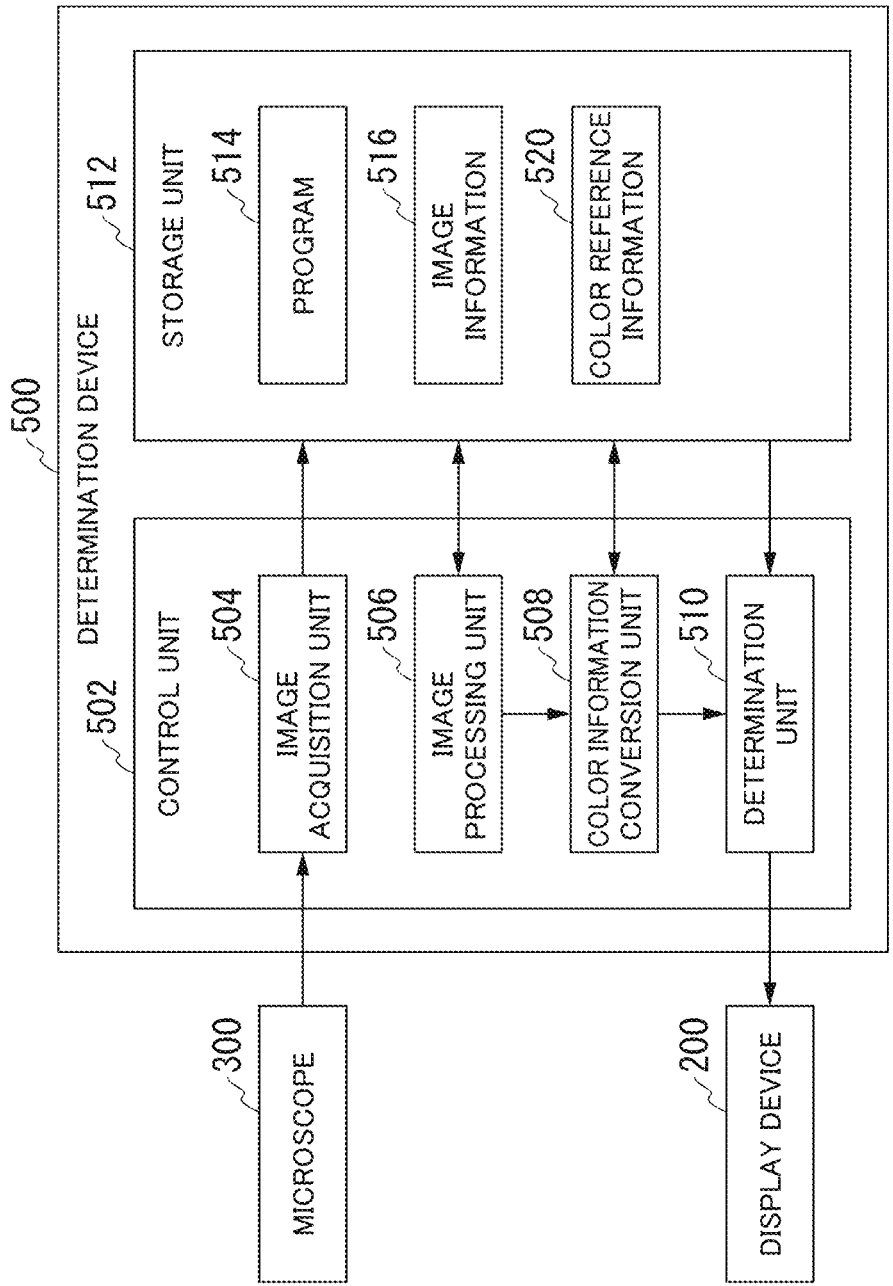
FIG. 21 is a diagram showing a determination system according to the present embodiment.

FIG. 21 shows the determination system 3 according to the present embodiment. The determination system 3 according to the present embodiment is different from the determination system 1 according to the first embodiment in a method of setting color reference information and a method of determining whether or not growth has progressed normally. The determination system 3 according to the present embodiment includes a determination device 500, a display device 200, and a microscope 300.

The determination device 500 acquires an enlarged image of a subject S provided by the microscope 300. After the enlarged image of the subject S is acquired, the determination device 500 determines whether or not the subject S has grown normally on the basis of color information of the subject S included in an image obtained by performing image processing on the enlarged image of the subject S with reference to color information in one or more growth processes of sample cells.

Here, the color information in one or more growth processes of the sample cells is pre-stored in the determination device 500. The determination device 500 displays a result of determining whether or not the subject S has grown normally on the display device 200. According to this configuration, the determination device 500 can allow the user to know a result of evaluating whether or not the subject S has grown normally.

<Configuration of Determination Device>

Next, a configuration of the determination device 500 will be described. The determination device 500 includes a control unit 502 and a storage unit 512.

The storage unit 512 pre-stores a program 514 that causes the control unit 502 to execute a process of determining whether or not cell growth has progressed normally, image information 516, and color reference information 520.

The image information 516 is image information of an enlarged image of the subject S acquired by the control unit 502. For example, as an example of a sample cell, a visual cell or an RPE cell changes to a light color, a red color, and a brownish-red color as the growth process progresses to differentiation induction or maturation from the time "immediately after seeding" or "immediately after differentiation induction."

The color reference information 520 stores color information in one or more growth processes of sample cells. Here, the color reference information 520 is color information of sample cells when a predetermined time period has elapsed from the time "immediately after seeding" or "immediately after differentiation induction" and is color information of sample cells that change with the progress of growth to a differentiation induction process or a cell maturation process. The color information included in the color reference information 520 includes information about a positive region. In the color reference information 520, for example, the elapsed time period from the time "immediately after seeding" or "immediately after differentiation induction" and the color information for the elapsed time period are stored in association or the trajectory of a sequential change in color information may be stored.

Further, information representing a positive region set on the basis of a result of plotting color information obtained by analyzing color information regarding Cb and color information regarding Cr in an image of each of one or more cells included in sample cells in a certain growth process in a color space expressed by Cb and Cr is stored in the color reference information 520.

<Method of Setting Color Reference Information 520>

Figure 22:
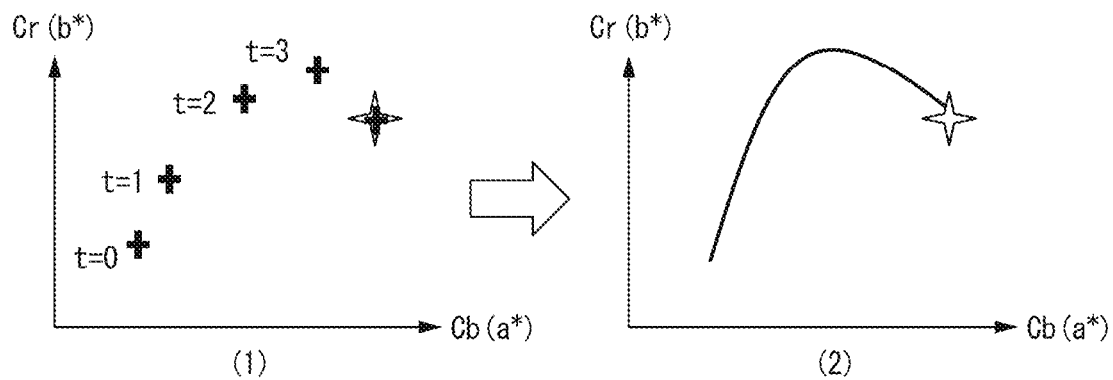
FIG. 22 is a diagram showing a process of determining subject growth.

FIG. 22 shows a method (part 5) of setting the color reference information 520. FIG. 22(1) shows a result of analyzing color information of an image of sample cells in a certain growth process and plotting the color information in a color space expressed by Cb and Cr. Here, the growth process represents that the sample cells change in a differentiation induction process or a cell maturation process from the time "immediately after seeding" or "immediately after differentiation induction." For example, the center of gravity of color information of an image of each of one or more cells is obtained on the basis of a result of analyzing color information regarding Cb and color information regarding Cr in an image of each of one or more cells included in sample cells in a certain growth process and the obtained center of gravity of the color information is plotted. Here, the center of gravity of the color information is an example and the determination device 500 can apply statistical values such as the mean value of the color information, a median value of the color information, and a mode value of the color information.

FIG. 22(2) shows an example in which a positive region is set on the basis of the center of gravity of the color information plotted in the color space expressed by Cb and Cr on the basis of FIG. 22(1). For example, the trajectory of the center of gravity of the color information shown in FIG. 22(1) is set as a positive region.

Although a case in which color information of an image of sample cells in a certain growth process is plotted in the color space expressed by Cb and Cr in FIGS. 22(1) and 22(2), the present invention is not limited thereto. For example, the present invention can also be applied to a case in which the color information of the image of the subject S in the certain growth process is plotted in a color space expressed by chromaticity (a*, b*) representing hue and saturation except for L* representing brightness within the L*a*b* color space described with reference to FIG. 4. The description will be continued with reference again to FIG. 21.

The control unit 502 is implemented by, for example, a CPU, and executes the program 514 stored in the storage unit 512, so that the control unit 502 functions as an image acquisition unit 504, an image processing unit 506, a color information conversion unit 508, and a determination unit 510.

The image acquisition unit 504 acquires an image of the subject S provided by the microscope 300 and stores the image in the image information 516 of the storage unit 512. For example, the image acquisition unit 504 periodically acquires the image of the subject S provided by the microscope 300 and stores image information of the subject S in the image information 516 of the storage unit 512. The image acquisition unit 504 may be configured to acquire information representing an elapsed time period from the time "immediately after seeding" or "immediately after differentiation induction" together with the image information of the subject S in the storage unit 512 and store the acquired information representing the elapsed time period in the image information 516 of the storage unit 512.

The image processing unit 506 acquires the image information of the subject S stored in the image information 516 of the storage unit 512 and executes image processing on the acquired image information of the subject S. An example of the image processing is color correction, color conversion, color adjustment, color tone adjustment, "edge detection" for finding a boundary of a physical object from a change in a concentration, or the like. For example, the image processing unit 506 performs image processing on the image information of the subject S acquired from the image information 516 of the storage unit 512.

The image processing unit 506 extracts a target for measuring the color information of the image obtained by performing the image processing. Specifically, the image processing unit 506 extracts one or more cells such as one or more cell clusters or one or more paving stone-shaped cells as a target for measuring color information from an image obtained by performing image processing. The image processing unit 506 outputs image information of one or more cells that have been extracted to the color information conversion unit 508.

The color information conversion unit 508 measures a color of the image obtained by the image information of each of the one or more cells supplied by the image processing unit 506. The color information conversion unit 508 obtains the center of gravity of the color information on the basis of one or more pieces of color information obtained by measuring a color of each of the one or more cells. Here, the center of gravity of the color information is an example and the color information conversion unit 508 may obtain statistical values of the color information such as a mean value of the color information, a median value of the color information, and a mode value of the color information on the basis of each of one or more pieces of color information obtained by measuring the color of the image of each of the one or more cells. Here, the description of a case in which the center of gravity of the color information is obtained will be continued. The color information conversion unit 508 outputs information representing the center of gravity of the color information to the determination unit 510.

The determination unit 510 determines whether or not the subject S has grown normally on the basis of the information representing the center of gravity of the color information supplied from the color information conversion unit 50M. For example, the determination unit 510 acquires information representing a positive region from the color reference information 520 of the storage unit 512 and determines whether or not the center of gravity of the color information supplied from the color information conversion unit 408 is on the same trajectory of the center of gravity of the color information of the image of the sample cell shown in FIG. 22(2) on the basis of the acquired information representing the positive region. The determination unit 510 determines that the subject S has grown normally when the center of gravity of the color information is on the trajectory of the center of gravity of the color information and determines that the subject S has not grown normally when the center of gravity is not on the trajectory of the center of gravity. The determination unit 510 outputs information representing a result of determining whether or not the subject S has grown normally to the display device 20. The description will be specifically given with reference to FIG. 23.

Figure 23:
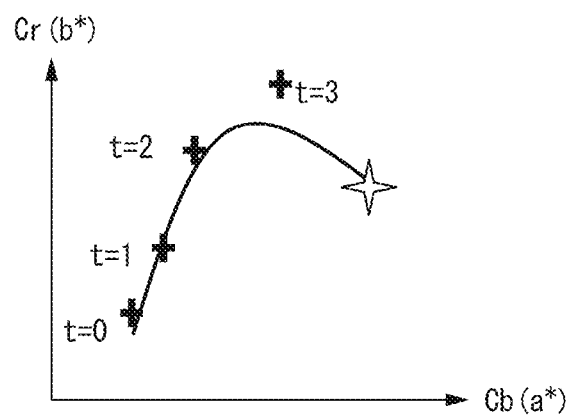
FIG. 23 is a diagram showing a process of determining subject growth.

FIG. 23 shows an example of a process of determining whether or not the center of gravity of the color information is on the trajectory of the center of gravity of the color information. In the example shown in FIG. 23, the determination unit 510 determines that the center of gravity is on the trajectory when t=0, 1, and 2 and determines that the center of gravity is not on the trajectory when t=3. In other words, the determination unit 510 determines that the subject S has grown normally when t=0, 1, and 2 and determines that the subject S has not grown normally when t=3.

<Operation of Determination Device>

Figure 24:
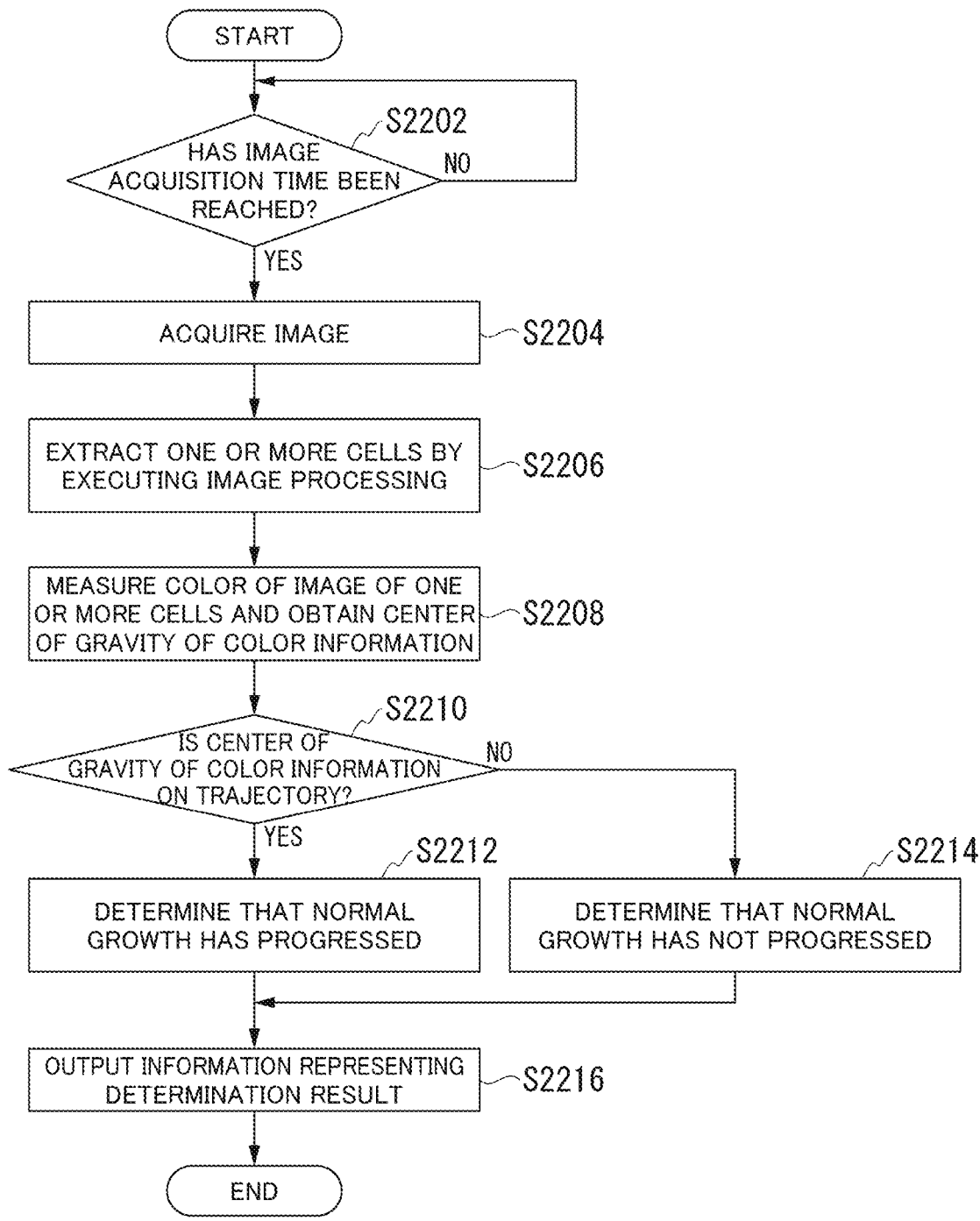
FIG. 24 is a flowchart showing an operation of the determination device according to the present embodiment.

FIG. 24 shows an example of an operation of the determination device 500 according to the present embodiment. A case in which the determination device 500 periodically acquires an image will be described with reference with FIG. 24. However, the present invention is not limited to this example and can also be applied to a case in which the determination device 500 non-periodically acquires an image.

Steps S1802 to S1808 of FIG. 20 can be applied as steps S2202 to S2208.

In step S2210, the determination unit 510 acquires information representing a positive region from the color reference information 520 of the storage unit 512 and determines whether or not the center of gravity of the color information of the image of one or more cells is on the trajectory of the center of gravity of the color information on the basis of the information representing the acquired positive region.

In step S2212, the determination unit 510 determines that normal growth has progressed when the center of gravity of the color information is on the trajectory of the center of gravity of the color information.

In step S2214, the determination unit 510 determines that growth has not progressed when the center of gravity of the color information is not on the trajectory of the center of gravity of the color information.

In step S2216, the determination unit 510 outputs information representing a determination result in step S2212 or information representing a determination result in step S2214. For example, when the information representing the determination result is output to the display device 200, the display device 200 displays the determination result.

Although an example in which the color information in one or more growth processes of the sample cells and the information representing the positive region included in the color reference information 520 are pre-stored has been described in the above-described embodiment, the present invention is not limited to this example.

For example, the color information in one or more growth processes of the sample cells and the information representing the positive region included in the color reference information 520 may be accumulated or updated on the basis of a result of measuring a color of an image obtained according to image information of one or more cells in the color information conversion unit 508.

According to this configuration, it is possible to accumulate or update color information in the growth process and information representing a positive region on the basis of the color measurement result. In this case, an accumulating process and an updating process may be executed by the control unit 502.

According to this configuration, the determination device 500 according to the present embodiment can perform a process without the color information in one or more growth processes of the sample cells and the information representing the positive region included in the color reference information 520 having been previously provided.

Also, in the above-described embodiment, when the color information conversion unit 508 may analyze color information of an image of each of one or more cells, the color information may be analyzed for each pixel. According to this configuration, the determination device 500 according to the present embodiment can perform analysis in a short time from the step before the form of one or more cells becomes clear.

The determination device according to the present embodiment acquires an enlarged image of the subject S and extracts one or more cells such as one or more cell clusters or one or more paving stone-shaped cells included in the subject S. The determination device obtains a statistical value on the basis of color information of the image of each of the one or more cells and determines whether the subject S has grown normally on the basis of whether the statistical value is on a preset trajectory of a statistical value of color information of sample cells when a predetermined time period has elapsed from the time "immediately after seeding" or "immediately after differentiation induction."

According to this configuration, the determination device according to the present embodiment can determine whether or not cell growth is normal in the process of culturing cells. Further, the determination device according to the present embodiment can further reduce a load of a calculation process than when it is determined whether or not color information is on a trajectory on the basis of color information of an image of each of one or more cells because a determination is made on the basis of whether or not a value of the center of gravity of the color information is on a preset trajectory of the center of gravity of the color information on the basis of the value of the center of gravity of the color information of the image of each of the one or more cells.

Fourth Embodiment

Figure 25:
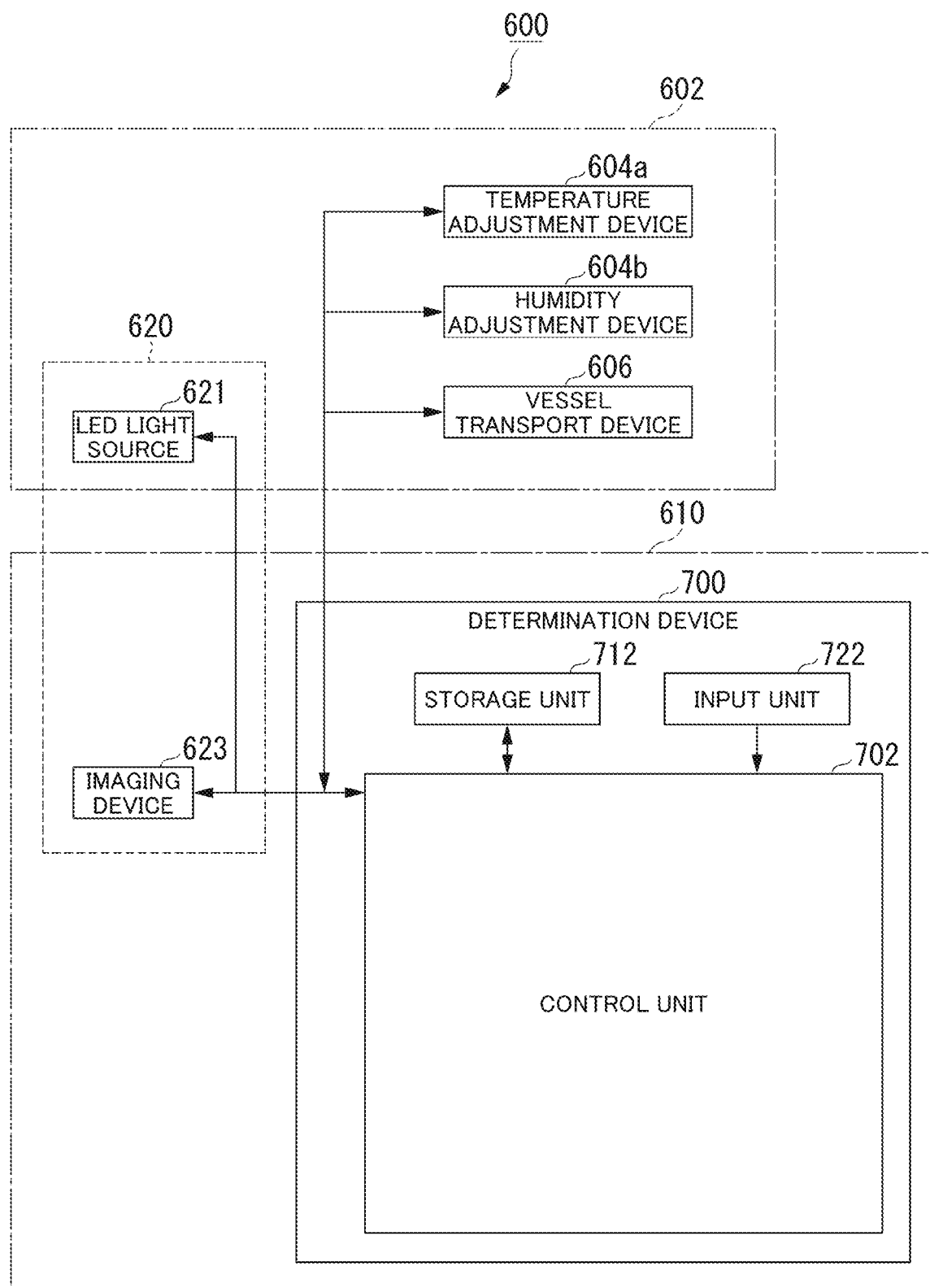
FIG. 25 is a block diagram showing an example of an observation device according to the present embodiment.
Figure 26:
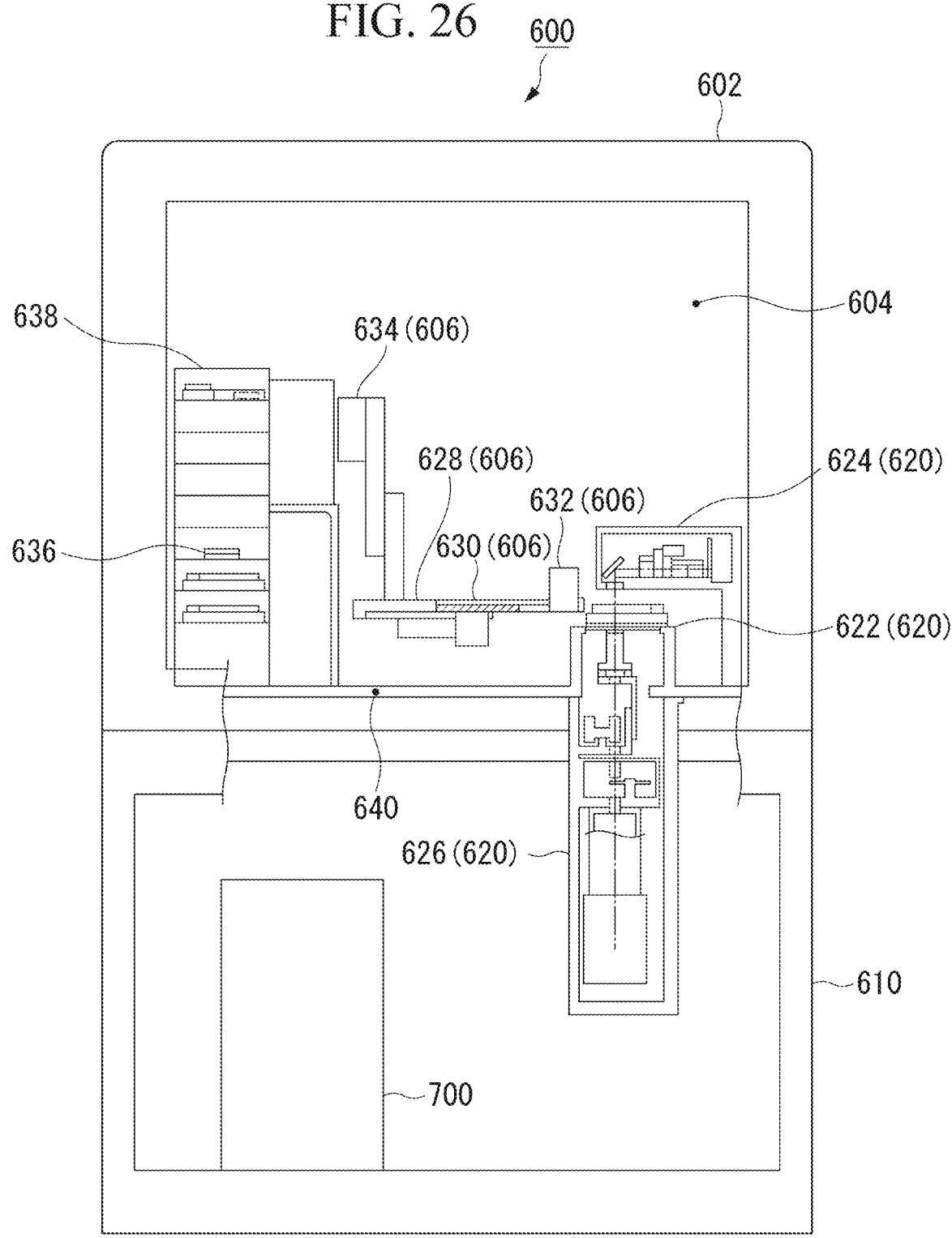
FIG. 26 is a front view of the observation device according to the present embodiment.
Figure 27:
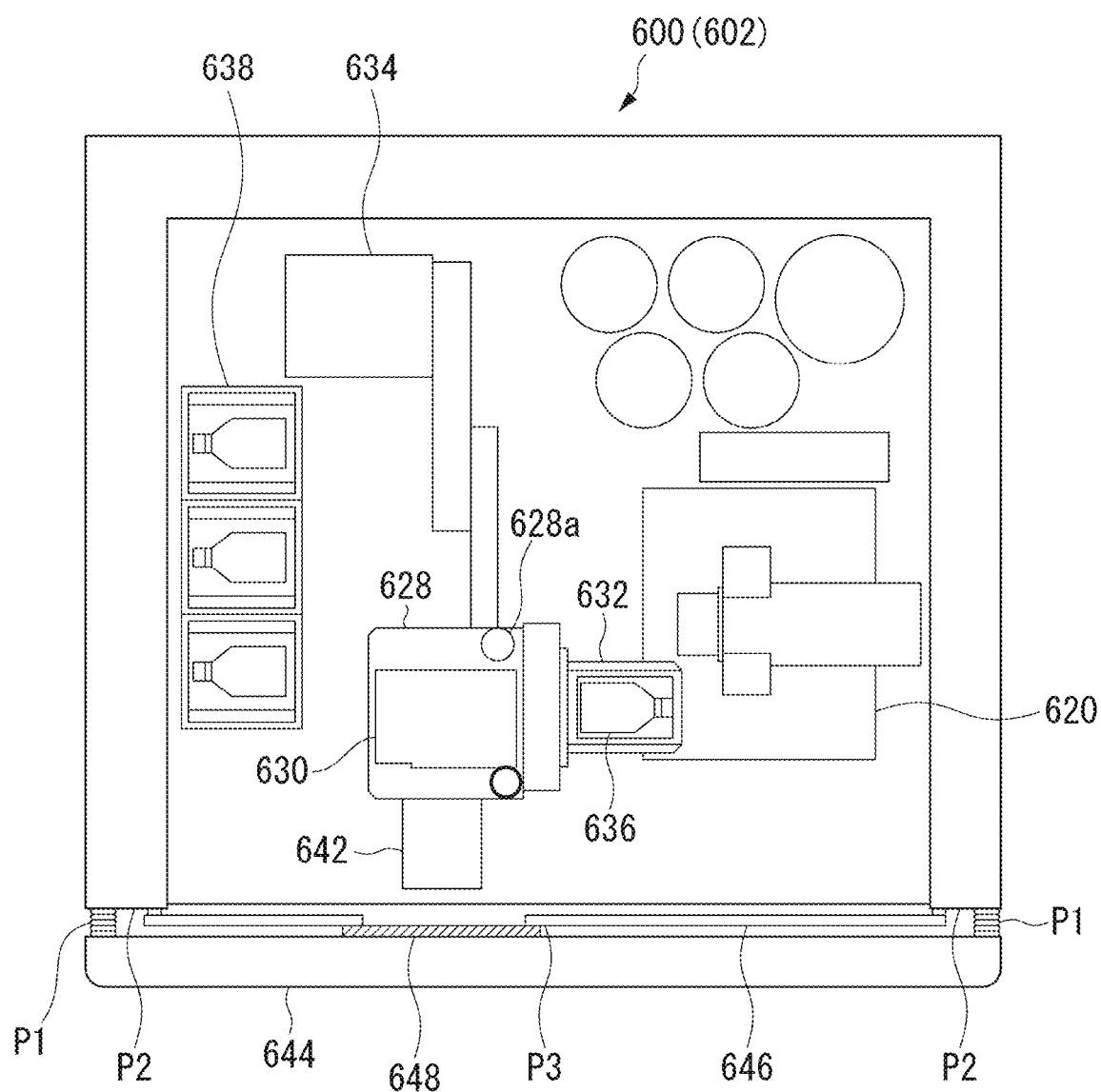
FIG. 27 is a plan view of the observation device according to the present embodiment.

A determination system according to the present embodiment will be described. The determination system according to the present embodiment is an incubator (an observation device) to which any one of the determination device 100, the determination device 400, and the determination device 500 described above is applied. An outline of a configuration of the incubator according to the present embodiment will be described. FIG. 25 is a block diagram showing an example of a configuration of an incubator 600 according to the present embodiment. FIGS. 26 and 27 are a front view and a plan view of the incubator 600 according to the present embodiment.

The incubator 600 is a device for culturing cells and imaging the cultured cells with a microscope camera to observe a state of the cells. The incubator 600 has an upper casing 602 and a lower casing 610. In an assembled state of the incubator 600, the upper casing 602 is placed on the lower casing 610. Also, an internal space between the upper casing 602 and the lower casing 610 is vertically partitioned by a base plate 640.

First, an outline of a configuration of the upper casing 602 will be described. Inside the upper casing 602, a homeothermic chamber 604 for culturing cells is formed. The homeothermic chamber 604 includes a temperature adjustment device 604a and a humidity adjustment device 604b and the inside of the homeothermic chamber 604 is maintained in an environment suitable for cell culture (for example, an atmosphere having a temperature of 37° C. and a humidity of 90%) (the illustration of the temperature adjustment device 604a and the humidity adjustment device 604b in FIG. 27 is omitted).

A large door 644, a middle door 646, and a small door 648 are disposed on a front surface of the homeothermic chamber 604. The large door 644 covers front surfaces of the upper casing 602 and the lower casing 610. The middle door 646 covers a front surface of the upper casing 602 and isolates the homeothermic chamber 604 from an external environment when the large door 644 is opened. The small door 648 is a door for carrying in and out a culture vessel 636 for culturing cells and is attached to the middle door 646. By carrying in and out the culture vessel 636 from the small door 648, it is possible to restrict an environmental change in the homeothermic chamber 604. Also, the airtightness of the large door 644, the middle door 646, and the small door 648 is maintained in by packings P1, P2, and P3, respectively.

Also, a stocker 638, an observation unit 620, a vessel transport device 606, and a transport table 642 are disposed in the homeothermic chamber 604. Here, the transport table 642 is disposed in front of the small door 648 and the culture vessel 636 is carried in and out from the small door 648.

The stocker 638 is disposed on a left side of the homeothermic chamber 604 when viewed from a front surface of the upper casing 602 (a lower side of FIG. 27). The stocker 638 includes a plurality of shelves and each shelf of the stocker 638 can store a plurality of culture vessels 636. Also, in each culture vessel 636, cells to be cultured are stored together with a medium.

The observation unit 620 is disposed on a right side of the homeothermic chamber 604 when viewed from the front surface of the upper casing 602. The observation unit 620 can perform time-lapse observation of cells within the culture vessel 636.

Here, the observation unit 620 is fitted and disposed in an opening of the base plate 640 of the upper casing 602. The observation unit 620 includes a sample table 622, a stand arm 624 projecting above the sample table 622, and a main body portion 626 in which a microscopic optical system for phase difference observation and an imaging device 623 are embedded. The sample table 622 and the stand arm 624 are disposed in the homeothermic chamber 604, while the main body portion 626 is stored within the lower casing 610.

The sample table 622 is made of a translucent material and the culture vessel 636 can be placed thereon. The sample table 622 is configured to be movable in a horizontal direction and can adjust a position of the culture vessel 636 placed on an upper surface thereof. Also, the stand arm 624 has a built-in LED light source 621. The imaging device 623 can acquire a microscopic image of the cells by imaging the cells of the culture vessel 636 transmitted and illuminated from above the sample table 622 by the stand arm 624 via the microscopic optical system.

The vessel transport device 606 is disposed at the center of the homeothermic chamber 604 when viewed from the front surface of the upper casing 602. The vessel transport device 606 transfers the culture vessel 636 from and to the stocker 638, the sample table 622 of the observation unit 620, and the transport table 642.

As shown in FIG. 27, the vessel transport device 606 has a vertical robot 634 having an articulated arm, a rotation stage 628, a mini stage 630, and an arm portion 632. The rotation stage 628 is attached to a distal end of the vertical robot 634 so that the rotation stage 628 is rotatable by 180° in the horizontal direction via the rotation shaft 628a. Thus, the rotation stage 628 can cause the arm portion 632 to face each of the stocker 638, the sample table 622, and the transport table 642.

Also, the mini stage 630 is slidably attached to the rotation stage 628 in the horizontal direction. The arm portion 632 for gripping the culture vessel 636 is attached to the mini stage 630.

Next, an outline of a configuration of the lower casing 610 will be described. Inside the lower casing 610, the main body portion 626 of the observation unit 620 and the determination device 700 are stored.

The determination device 700 is connected to each of the temperature adjustment device 604a, the humidity adjustment device 604b, the observation unit 620, and the vessel transport device 606. The determination device 700 generally controls each part of the incubator 600 in accordance with a predetermined program.

As an example, the determination device 700 controls each of the temperature adjustment device 604a and the humidity adjustment device 604b so that the inside of the homeothermic chamber 604 is maintained under predetermined environmental conditions. Also, the determination device 700 controls the observation unit 620 and the vessel transport device 606 on the basis of a predetermined observation schedule so that an observation sequence of the culture vessel 636 is automatically executed. Further, the determination device 700 executes a cultured state evaluation process of evaluating a cultured state of the cells on the basis of an image acquired in the observation sequence.

Figure 28:
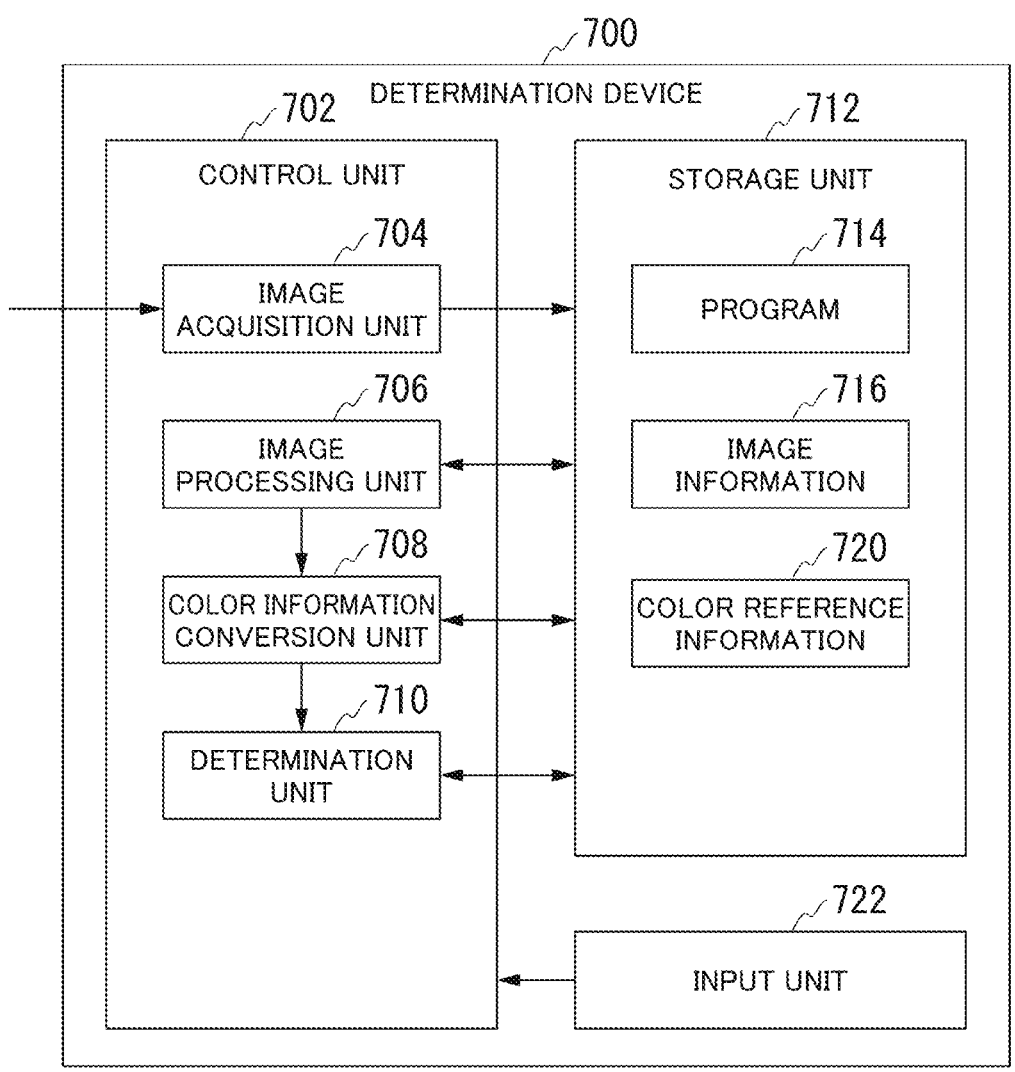
FIG. 28 is a diagram showing the determination device according to the present embodiment.

FIG. 28 shows the determination device 700 according to the present embodiment. The determination device 700 has a control unit 702, a storage unit 712, and an input unit 722.

The storage unit 712 includes a hard disk, a non-volatile storage medium such as a flash memory, and a volatile storage medium such as a DRAM or an SRAM. The storage unit 712 stores management data regarding each culture vessel 636 stored in the stocker 638, data of an overall observation image captured by the imaging device, and data of a microscope image. Further, the storage unit 712 stores a program 714 to be executed by the control unit 702. Also, various calculation results from the control unit 702 are temporarily stored in the storage unit 712.

Also, the above-described management data includes (a) index data indicating individual culture vessels 636, (b) a storage position of the culture vessel 636 in the stocker 638, (c) a type and a shape of the culture vessel 636 (a well plate, a dish, a flask, or the like), (d) a type of cell being cultured in the culture vessel 636 (information for identifying a cell line), (e) an observation schedule of the culture vessel 636, (f) imaging conditions during time lapse observation (magnification of an objective lens, an observation point within the vessel, and the like), and the like. Also, management data is generated for each small vessel with respect to the culture vessel 636 where cells can be simultaneously cultured in a plurality of small vessels such as well plates.

Also, in the present embodiment different types of cell lines are observed as cell lines to be observed. In this case, information for identifying the cell line is required. However, when there is only one cell line to be observed, it is not necessary to identify the cell line and cell line identification information is not essential. Of course, information representing the cell line may be supplied even if only one cell line is observed.

Also, when different types of cell lines are observed, it is preferable to store cell line information for identifying the cell line of the cell in the storage unit 712 and store the cell line information in association with other information.

In addition to the program 714, the image information 716 and the color reference information 720 are stored in the storage unit 712.

Any one of the image information 116, the image information 416, and the image information 516 in the above-described embodiment can be applied as the image information 716. Also, any one of the color reference information 120, the color reference information 420, and the color reference information 520 in the above-described embodiment can be applied as the color reference information 720.

The input unit 722 includes an input device such as a keyboard and a mouse. Various information such as cell line information is supplied to the input unit 722 according to an operation of the user.

A configuration of the control unit 702 will be described. The control unit 702 includes an image acquisition unit 704, an image processing unit 706, a color information conversion unit 708, and a determination unit 710.

Any one of the image acquisition unit 104, the image acquisition unit 404, and the image acquisition unit 504 in the above-described embodiments can be applied as the image acquisition unit 704. Also, anyone of the image processing unit 106, the image processing unit 406, and the image processing unit 506 in the above-described embodiments can be applied as the image processing unit 706. Also, any one of the color information conversion unit 108, the color information conversion unit 408, and the color information conversion unit 508 in the above-described embodiments can be applied as the color information conversion unit 708. Also, any one of the determination unit 110, the determination unit 410, and the determination unit 510 in the above-described embodiment can be applied as the determination unit 710.

<Operation of Incubator>

Figure 29:
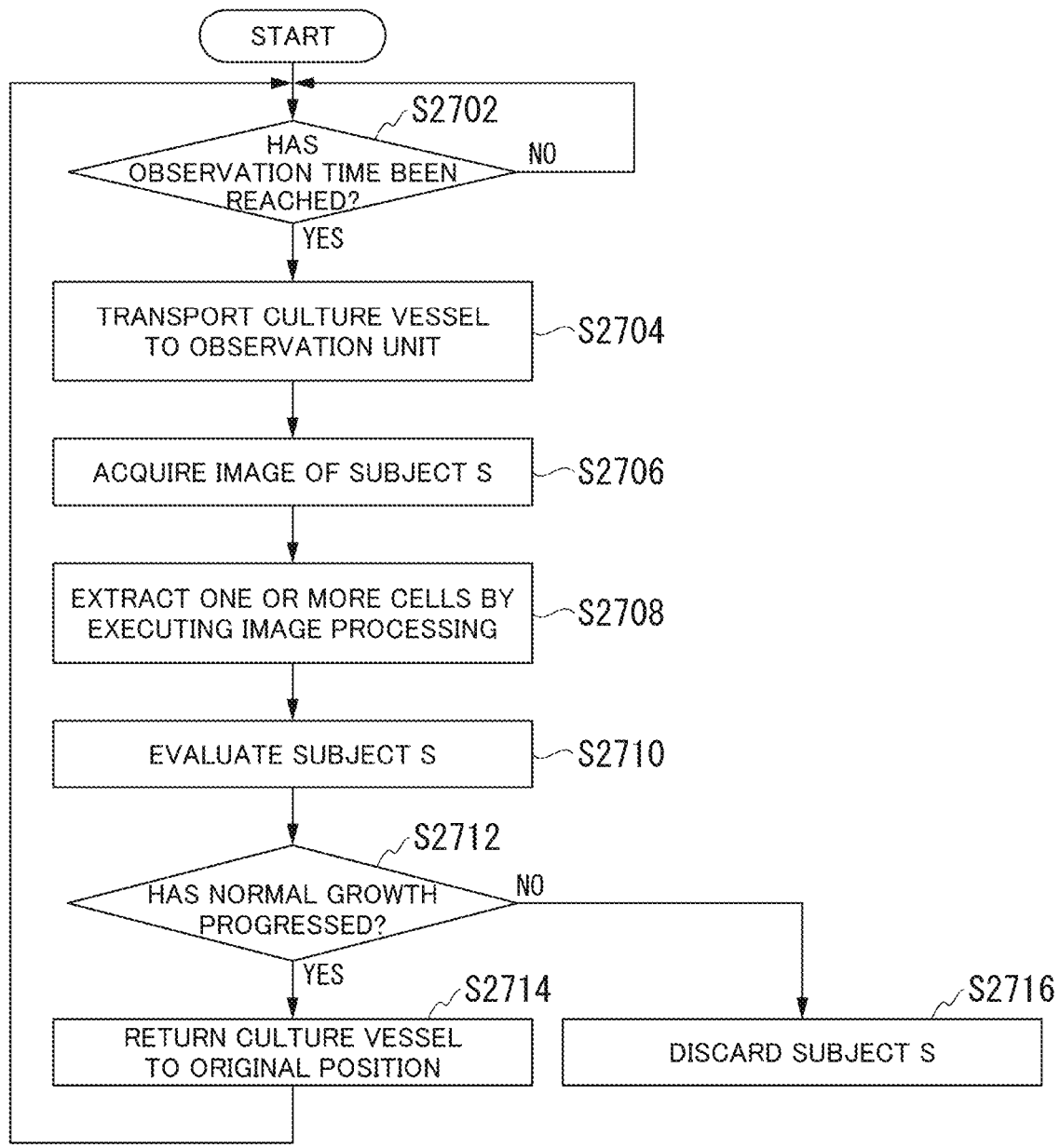
FIG. 29 is a flowchart showing an operation of the observation device according to the present embodiment.

An operation of the incubator 600 according to the present embodiment will be described with reference to FIG. 29. FIG. 29 shows an example of the operation of the incubator 600 according to the present embodiment. An example in which the determination device 700 mounted in the incubator 600 periodically acquires an image of a subject S and determines whether or not the subject S has grown normally will be described with reference to FIG. 29. However, the present invention is not limited to the above example and can also be applied to a case in which the determination device 700 non-periodically acquires an image of the subject S and determines whether or not the subject S has grown normally.

In step S2702, the control unit 702 compares an observation schedule of the management data of the storage unit 712 with a current date and time and determines whether or not an observation start time of the culture vessel 636 has been reached. When the observation start time has been reached (YES side), the control unit 702 moves the process to step S2704. On the other hand, when the observation time of the culture vessel 636 has not been reached (NO side), the control unit 702 waits until the time of the next observation schedule.

In step S2704, the control unit 702 instructs the vessel transport device 606 to perform the transport of the culture vessel 636 corresponding to the observation schedule. The vessel transport device 606 carries out the culture vessel 636 of the instruction from the stocker 638 and places the culture vessel 636 on the sample table 622 of the observation unit 620. Also, in the step in which the culture vessel 636 is placed on the sample table 622, a bird view camera (not shown) built in the stand arm 624 captures an overall observation image of the culture vessel 636. Thereby, an image of the culture vessel 636 is captured.

In step S2706, the image acquisition unit 704 of the control unit 702 acquires the image of the culture vessel 636 captured in step S2704.

In step S2708, the image processing unit 706 of the control unit 702 processes image information of the image acquired by the image acquisition unit 704 and extracts a color measurement target by extracting one or more cells such as cell clusters and paving stone-shaped cells.

In step S2710, the color information conversion unit 708 and the determination unit 710 of the control unit 702 evaluate the subject S. Anyone of the process of steps S1108 and S1110 in FIG. 11, the process of steps S1808 to S1812 in FIG. 20, and the process of steps S2208 and S2210 in FIG. 24 can be applied as a process of evaluating the subject S.

In step S2712, the determination unit 710 of the control unit 702 determines whether or not the subject S has grown normally.

In step S2714, the control unit 702 instructs the vessel transport device 606 to perform the transport of the culture vessel 636 when the subject S has grown normally. The vessel transport device 606 carries out the culture vessel 636 of the instruction from the sample table 622 of the observation unit 620 and returns the culture vessel 636 to the stocker 638.

In step S2716, the control unit 702 instructs the vessel transport device 606 to perform the transport of the culture vessel 636 to the small door 648 when the subject S has not grown normally. The vessel transport device 606 transports the culture vessel 636 of the instruction from the sample table 622 of the observation unit 620 to a position of the small door 648. The user opens the small door 648 and takes out the culture vessel 636. The user discards the subject S that has not grown normally. Subsequently, the control unit 702 ends an observation sequence and returns the process to step S2702.

Steps S2702 to S2716 are iterated as many times as the number of subjects S. The determination device 700 according to the present embodiment can determine whether or not cell growth is normal in the process of culturing the cells and can discard the subject S that has not grown normally. According to this configuration, the determination device 700 according to the present embodiment can finally leave the subject S which has grown normally.

In the incubator according to the present embodiment, a stocker for storing the culture vessel 636 storing the subject S that has not grown normally may be provided. In this case, the control unit 702 instructs the vessel transport device 606 to transport the culture vessel 636 when the subject S has not grown normally. The vessel transport device 606 carries out the culture vessel 636 of the instruction from the sample table 622 of the observation unit 620 and returns the culture vessel 636 to the stocker that stores the subject S that has not grown normally. According to this configuration, the user does not need to discard the subject S that has not grown normally every time the subject S is detected.

Also, the various processes described above may be performed by recording a program for executing processes of the incubator 600 (the observation device) according to the present embodiment on a computer-readable recording medium and causing a computer system to read and execute the program recorded on the recording medium.

Also, the "computer system" used here is assumed to include an operating system (OS) and hardware such as peripheral devices. Also, the "computer system" is assumed to include a homepage providing environment (or displaying environment) when a World Wide Web (WWW) system is used. Also, the "computer-readable recording medium" refers to a storage device, including a flexible disk, a magneto-optical disc, a read only memory (ROM), a writable non-volatile writable memory such as a flash memory, a portable medium such as a compact disc (CD)-ROM, and a hard disk embedded in the computer system.

Further, the "computer-readable recording medium" is assumed to include a computer-readable recording medium for retaining the program for a predetermined time period as in a volatile memory (a dynamic random access memory (DRAM)) inside the computer system including a server and a client when the program is transmitted via a network such as the Internet or a communication circuit such as a telephone circuit. Also, the above-described program may be transmitted from a computer system storing the program in a storage device or the like via a transmission medium or transmitted to another computer system by transmission waves in a transmission medium.

Here, the "transmission medium" for transmitting the program refers to a medium having a function of transmitting information as in a network (a communication network) such as the Internet or a communication circuit (a communication line) such as a telephone circuit. Also, the above-described program may be a program for implementing some of the above-described functions. Further, the above-described program may be a program capable of implementing the above-described function in combination with a program already recorded on the computer system, i.e., a so-called differential file (differential program).

Although a case in which a type of cell exhibiting a color tone is used as an example of the subject S has been described in the above-described embodiment, the present invention is not limited thereto. For example, the subject S may be a cell subjected to a staining process. This staining process will be described in consideration of a case in which the cells are animal cells as an example. In the staining process, for example, a pigment such as trypan blue is dropped onto the cells. Because the cell membrane of dead cells is damaged, the pigment easily penetrates into the cells as compared with living cells. Thus, trypan blue selectively penetrates into dead cells among living cells and dead cells. That is, when cells are stained with trypan blue, live cells are not stained and dead cells are stained blue.

Although the staining with trypan blue has been described here as an example of the staining process, the present invention is not limited thereto. As long as it is a pigment that can selectively stain live cells and dead cells, the cells may be stained with a pigment other than trypan blue.

Here, if the cell to be subjected to the staining process is a cell having no pigment, it can be easily determined whether the cell is a living cell or a dead cell by determining the hue of the cell.

Although embodiments of the present invention have been described above in detail with reference to the drawings, specific configurations are not limited to the embodiments and other designs and the like may also be included without departing from the spirit and scope of the present invention.

REFERENCE SIGNS LIST

100 Determination device
102 Control unit
112 Storage unit
114 Program
116 Image information
120 Color reference information
300 Microscope
400 Determination device
402 Control unit
412 Storage unit
414 Program
416 Image information
420 Color reference information
500 Determination device
502 Control unit
512 Storage unit
514 Program
516 Image information
520 Color reference information
600 Incubator
700 Determination device
702 Control unit
712 Storage unit
714 Program
716 Image information
720 Color reference information

What is claimed is:

1. A cell state evaluation device comprising:
a processor;
a memory encoded with instructions executed by the processor, the instructions causing the processor to perform operations comprising:
calculating color information of at least one or a combination of hue, saturation, or lightness in the color space of an image of one captured cell or a plurality of captured cells in a captured image;
determining a cultured state of the cell on the basis of the color information and color reference information;
storing a positive region set on the basis of the color information of the image of one sample cell or a plurality of sample cells in the color space as the color reference information which is the determination standard; and
obtaining a positive rate which is a proportion of color information included in the positive region and served as color measurement targets on the basis of the color information and the positive region,
wherein the positive region is a color region in the color space into which the one sample cell or a plurality of sample cells change as growth progresses to the differentiation induction process of the cell maturation process, and
wherein the determining includes determining the growth process of the one captured cell or a plurality of captured cells in the cultured state on the basis of the positive rate.

2. The cell state evaluation method according to claim 1, wherein the positive rate which is a ratio of the number of cells or a ratio of the area of the region included in the positive region and served as the color measurement targets.

3. The cell state evaluation device according to claim 1, wherein the determining includes determining on the basis of the change over time of the positive rate that the cell growth has progressed normally when the positive rate has increased compared to the previously determined positive rate, and determines that the cell growth has not progressed normally when the positive rate has not increased.

4. The cell state evaluation device according to claim 1, further comprising:
outputting information to display positive indicating positive region and negative indicating region which is not included in the positive region among regions serving as color measurement targets, and non-target indicating region other than the regions to a display device.

5. A microscope device comprising:
the device according to claim 1; and
a microscope configured to provide the device with the captured image periodically.

6. A cell state evaluation device comprising:
a processor;
a memory encoded with instructions executed by the processor, the instructions causing the processor to perform operations comprising:
calculating color information of at least one or a combination of hue, saturation, or lightness in the color space of an image of one captured cell or a plurality of captured cells in a captured image;
determining the cultured state of the cell or cells on the basis of the color information and color reference information;
storing a positive region set on the basis of the color information of the image of one sample cell or a plurality of sample cells in the color space as the color reference information which is the determination standard; and
obtaining a center of gravity of the color information or a statistic of the color information on the basis of the color information of the plurality of captured cells,
wherein the determining includes determining the cultured state of the one captured cell or a plurality of captured cells by determining whether or not the trajectory of the center of gravity or the statistic of the color information is on the same trajectory of the center of gravity or the statistic of the color information of the one sample cell or a plurality of sample cells in the color space on the basis of the color reference information representing the positive region.

7. The cell state evaluation device according to claim 6, further comprising:
outputting a determination result of whether or not the one captured cell or the plurality of captured cells are growing normally on the basis of the positive region to a display device as the cultured state of the cells.

8. The cell state evaluation device according to claim 6, wherein the cultured state of a cell is a differentiated state or a matured state of the cell.

9. A microscope device comprising:
the device according to claim 6; and
a microscope configured to provide the device with the captured image periodically.

10. A cell state evaluation device comprising:
a processor;
a memory encoded with instructions executed by the processor, the instructions causing the processor to perform operations comprising:
calculating color information of a least one or a combination of hue, saturation, or lightness in the color space of an image of one captured cell or a plurality of captured cells in a captured image;
determining the cultured state of the cell or cells on the basis of the color information and color reference information;
storing a reference value for determining positive type, which is set on the basis of the color information of the image of one sample cell or a plurality of sample cells in the color space as the color reference information which is the determination standard;
obtaining a center of gravity of the color information or a statistic of the color information on the bases of the color information of the plurality of cells; and
calculating a distance between the center of gravity or the statistic of the color information and the reference value,
wherein the determining includes determining the culture state of the one or a plurality of captured cells on the basis of the increase or decrease in the distance.

11. The cell state evaluation device according to claim 10, wherein the reference value is the center of gravity or the statistic of the color information of the image of the sample cells.

12. The cell state evaluation device according to claim 10, further comprising:
outputting a determination result of whether or not the one captured cell or the plurality of captured cells are growing normally on the basis of the calculated distance to a display device as the culture state of the cells.

13. The cell state evaluation device according to claim 10, wherein the determining includes determining that the once captured cell or the plurality of captured cells are growing normally when the calculated distance decreases.

14. The cell state evaluation device according to claim 10, wherein the color reference information is information in which the elapsed time of the growth process of the one sample cell or a plurality of sample cells and the color information in the elapsed time are in association.

15. The cell state evaluation device according to claim 10, wherein the cultured state of a cell is a differentiated state or a matured state of the cell.

16. A microscope device comprising:
the device according to claim 10; and
a microscope configured to provide the device with the captured image periodically.

\* \* \* \* \*